(12) United States Patent
Mickel et al.

(10) Patent No.: US 7,973,175 B2
(45) Date of Patent: Jul. 5, 2011

(54) SYNTHESIS OF RENIN INHIBITORS INVOLVING A CYCLOADDITION REACTION

(75) Inventors: Stuart J Mickel, Lausen (CH); Wolfgang Marterer, Freiburg i. B. (DE)

(73) Assignee: Novartis AG, Basel (CH)

( * ) Notice: Subject to any disclaimer, the term of this patent is extended or adjusted under 35 U.S.C. 154(b) by 202 days.

(21) Appl. No.: 12/067,055

(22) PCT Filed: Sep. 26, 2006

(86) PCT No.: PCT/EP2006/009323
§ 371 (c)(1),
(2), (4) Date: Mar. 17, 2008

(87) PCT Pub. No.: WO2007/039183
PCT Pub. Date: Apr. 12, 2007

(65) Prior Publication Data
US 2008/0255369 A1    Oct. 16, 2008

(30) Foreign Application Priority Data

Sep. 28, 2005  (GB) .................................. 0519764.5

(51) Int. Cl.
*C07D 207/00* (2006.01)
(52) U.S. Cl. ....................................................... 548/532
(58) Field of Classification Search ................... 548/532
See application file for complete search history.

(56) References Cited

U.S. PATENT DOCUMENTS 5,559,111 A    9/1996   Goeschke et al.
6,476,268 B1   11/2002  Winsel et al.

FOREIGN PATENT DOCUMENTS
EP           0 168 607        1/1986

OTHER PUBLICATIONS

Ayerbe et al., "Stereocontrolled synthesis of highly substituted praline esters via [3+2] cycloaddition between N-metalated azomethine ylides and nitroalkenes. Origins of the metal effect on the stereochemical outcome" J. Org. Chem. 63, pp. 1795-1805 (1998).
Hanessian et al., "The power of visual imagery in synthesis planning, stereocontrolled approaches to CGP-60536B, a potent renin inhibitor", J. Org. Chem. 67, pp. 4261-4274 (2002).
Mealy et al., "Aliskiren Fumarate", Drugs of the Future, 26 (12), pp. 1139-1148 (2001).
Meyer et al., "A short synthesis of polysubstituted pyrrolidines via α-(alkylidene-amino)nitriles", SYNLETT, No. 5, pp. 787-790 (2004).
Nyerges et al., "Silver acetate-catalysed asymmetric 1,3-dipolar cycloadditions of imines and chiral acrylamides," Tetrahedron, vol. 61, No. 15, pp. 3745-3753 (2005).
Coldham et al., "Intramolecular Dipolar Cycloaddition Reactions of Azomethine Ylides," Chem. Rev., vol. 105, pp. 2765-2809 (2005).
Husinec et al., "Chiral catalysts in the stereoselective synthesis of pyrrolidine derivatives via metallo-azomethine ylides," Tetrahedron: Asymmetry 16, pp. 2047-2061 (2005).

*Primary Examiner* — Rebecca L Anderson
*Assistant Examiner* — Samantha L Shterengarts
(74) *Attorney, Agent, or Firm* — Stephen Johnson; Lisa Matovcik

(57) ABSTRACT

The invention related to a novel process, novel process steps and novel intermediates useful in the synthesis of pharmaceutically active compounds, especially renin inhibitors, such as Aliskiren. Inter alia, the invention relates to a process for the manufacture of a compound of the formula III,

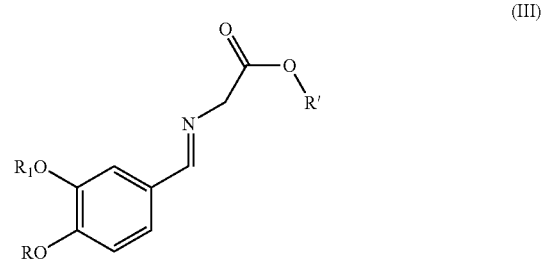

(III)

wherein R, $R_1$, and R' are as defined in the specification, or a salt thereof, and a compound of formula IV

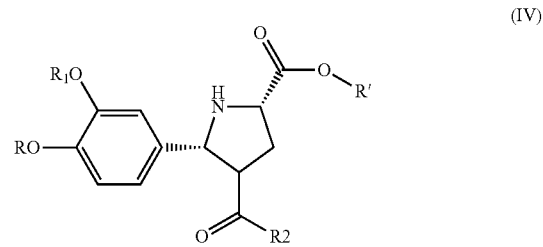

(IV)

wherein R, $R_1$, $R_2$ and R' are as defined in the specification, and processes of manufacturing these.

19 Claims, No Drawings

SYNTHESIS OF RENIN INHIBITORS INVOLVING A CYCLOADDITION REACTION

FIELD OF THE INVENTION

The invention relates to a novel process, novel process steps and novel intermediates useful in the synthesis of pharmaceutically active compounds, especially renin inhibitors.

BACKGROUND OF THE INVENTION

Renin passes from the kidneys into the blood where it affects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

With compounds such as (with INN name) aliskiren ((2S,4S,5S,7S)-5-amino-N-(2-carbamoyl-2-methylpropyl)-4-hydroxy-2-isopropyl-7-[4-methoxy-3-(3-methoxypropoxy)benzyl]-8-methylnonanamide), a new antihypertensive has been developed which interferes with the renin-angiotensin system at the beginning of angiotensin II biosynthesis.

As the compound comprises 4 chiral carbon atoms, the synthesis of the enantiomerically pure compound is quite demanding. Therefore, amended routes of synthesis that allow for more convenient synthesis of this sophisticated type of molecules are welcome.

It is therefore a problem to be solved by the present invention to provide new synthesis routes and new intermediates allowing a convenient and efficient access to this class of compounds.

In the search for more convenient ways to manufacture renin inhibitors such as aliskiren, it was found that pyrrolidines as shown below and derivatives thereof can be very useful intermediates in the synthesis of such renin inhibitors.

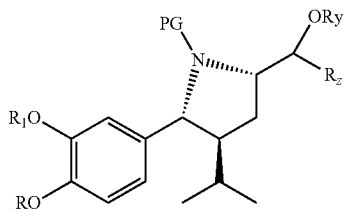

wherein
R is hydrogen, alkyl or alkoxyalkyl;
$R_1$ is hydrogen, alkyl or alkoxyalkyl;
Ry is hydrogen or preferably a hydroxyl protecting group;
$R_z$ is hydrogen or unsubstituted or substituted alkyl; and
PG is an amino protecting group, especially one removable by hydrolysis, e.g. lower alkoxycarbonyl, such as tert-butoxycarbonyl or benzyloxycarbonyl.

These pyrrolidines and methods to synthesize renin inhibitors are described in detail in GB application no. 0511686.8 and in the resulting PCT application PCT/EP2006/005370. The pyrrolidine ring locks the stereochemistry for subsequent conversions yielding eventually the amine and hydroxy moieties with the desired stereochemistry. However, although this process works well and has certain advantages, the pyrrolidine intermediates are prepared from amino alcohol compounds of the following formula

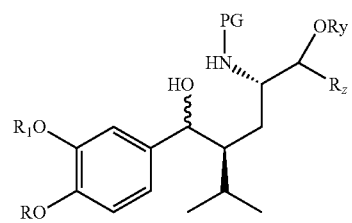

These compounds are accessible using a rather lengthy synthesis starting from pyroglutamic acid. Reference is made to PCT application EP2005/009347 published as WO2006/024501 where ketone amino derivatives of such compounds are prepared that can be converted into the respective amino alcohol.

SUMMARY OF THE INVENTION

It has now been found that useful pyrrolidine intermediates are accessible via a much shorter route, thus reducing the number of total steps to yield suitable renin inhibitors quite considerably.

In a first and very relevant aspect, the invention relates to a process for the manufacture of a compound of the formula III,

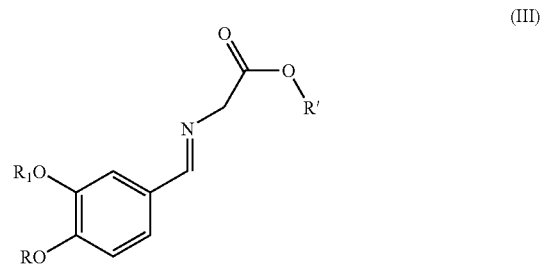

wherein
R is hydrogen, alkyl or alkoxyalkyl;
$R_1$ is hydrogen, alkyl or alkoxyalkyl; and
R' is hydrogen, alkyl or aralkyl;
or a salt thereof;
said manufacture comprising (preferably consisting of) reacting a compound of the formula I,

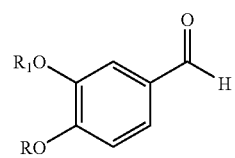

wherein R and $R_1$, are as defined for a compound of the formula III, with a glycine compound of formula II

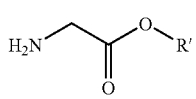
(II)

wherein R' is as defined for a compound of the formula III, in order to give the imine functionality. This process step as such, as well as a compound of the formula III (and its preferred embodiments as described later), or a salt thereof, also form embodiments of the invention.

Both reagents of formula I and II are either commercially available from suppliers such as Aldrich or Fluka, or they can be obtained by methods well known in the art. For example the aldehyde of formula I can be prepared according to the methods disclosed in Goeschke R. et al, Helv. Chimica Acta, 2003, 86(8), 2848 and Goeschke R. EP-A-678503.

The imine formation proceeds by any known method in order to obtain the compound of formula III. Preferably the reaction is conducted under basic or acidic conditions, more preferably basic conditions. Suitable bases include organic or inorganic bases, preferably organic bases, more preferably a nitrogen base, yet more preferably a tertiary nitrogen base. Examples of the tertiary nitrogen base include trimethylamine, DBU and triethylamine diisopropylethylamine. The reaction can be conducted in any suitable solvent, preferably an aprotic solvent such as an aromatic or a halogenated solvent, more preferably methylene chloride or toluene. Suitably the reaction is conducted so as to remove any water formed during the reaction, preferably water is removed concomitantly. Suitable means to remove the water include any drying agents, such as magnesium sulfate or sodium sulfate, or molecular sieves or azeotropic distillation. The reaction time and the temperature are chosen so as to bring the reaction to completion at a minimum time without the production of unwanted side products. Typically the reaction can be conducted at 0° C. to reflux, preferably 0 to 40° C., more preferably 15-30° C., such as room temperature, for 1 h to 48 h, preferably 5 h to 36 h, most preferably 17 to 30 h, such as 24 h.

Another important embodiment of the invention relates to a compound of the formula III as defined above, or a salt thereof. A compound of the formula III may be used, inter alia, for the synthesis of pharmaceutically active substances, preferably renin inhibitors such as aliskiren, especially as described in the following.

In a preferred further embodiment of the invention, this synthesis comprises as a further step or as individual synthesis the manufacture of a compound of formula IV

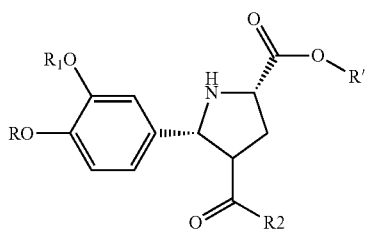
(IV)

wherein R, $R_1$ and R' are as defined for a compound of the formula III above and wherein $R_2$ is alkyl, or a salt thereof, in order to form the pyrrolidine ring, said manufacture comprising (preferably consisting of)

subjecting a compound of the formula III, especially synthesized as in the preceding step, to a cycloaddition reaction with an α,β-unsaturated carbonyl species of formula (V)

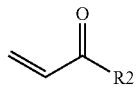
(V)

wherein $R_2$ is as defined for a compound of the formula IV above. This process step as such, as well as a compound of the formula IV (and its preferred embodiments as described later), or a salt thereof, also form embodiments of the invention.

The cycloaddition is typically a 1,3-dipolar cycloaddition reaction. It proceeds by any known method in order to obtain the compound of formula IV. In particular reference is made to the following literature references describing cycloaddition reactions: Coldham I and Hufton R., Chem. Rev., 2005, 105, 2765-2810, Husinec S and Savic, V., Tetrahedron Asymmetry 2005, 16, 2047-2061, Barr D. A. et al, Tetrahedron, 51, 273-294, Dikshit D. K. et al Tetrahedron Letters 2001, 42, 7891-7892, Nyerges M., et al Synthesis, 2002, 1823-1828, Garner, P. et al, Tetrahedron Letters, 2005, 46, 5181-5185 all of which are incorporated herein by reference. With respect to Coldham I and Hufton R. it is referred to chapter 3 specifically where various methods of using imine starting materials are described, in particular prototropy and metalation, of which metalation is preferred. Thus, any of the methods described in chapter 3.2 are particularly suitable and are incorporated herein by reference.

Preferably the reaction is conducted under basic conditions. Suitable bases include organic or inorganic bases, preferably organic bases more preferably a nitrogen base, yet more preferably a tertiary nitrogen base. Examples of the tertiary nitrogen base include triethylamine, DBU, diisopropylethylamine, quinine, TMEDA and trimethylamine. The reaction can be conducted in any suitable solvent, preferably an aprotic solvent such as an aromatic, etheric or a halogenated solvent, more preferably methylene chloride, DMSO, acetonitrile, tetrahydrofuran or toluene. Furthermore the reaction is preferably conducted in the presence of a suitable catalyst such as a metal catalyst. Suitable metal catalysts are described in the above cited references. The metal catalyst is typically a salt, preferably a Li, Ag, Cu, Zn, Co and Mn salt, such as a $Li^I$, $Ag^I$, $Cu^{II}$, $Zn^{II}$, $Co^{II}$ and $Mn^{II}$ salt, more preferably a Cu or Ag salt. The anion can be any suitable anion known in the art such as a halide, including chlorine and fluorine, trifluoromethanesulfonate (triflate or OTf) and acetate (OAc). Thus suitable metal catalysts include AgF, AgOAc, AgOTf, LiBr, $Cu(OTf)_2$, $Zn(OTf)_2$, $Zn(OAc)_2$, $CoCl_2$, $CoBr_2$, $MnBr_2$, more preferably AgOAc, AgOTf, $Cu(OTf)_2$ and $Zn(OTf)_2$, yet more preferably AgF, AgOAc or AgOTf, most preferably AgOAc. The reaction time and the temperature are chosen so as to bring the reaction to completion at a minimum time without the production of unwanted side products. Typically the reaction can be conducted at −70° C. to reflux, preferably 0 to 40° C., more preferably 15-30° C., such as room temperature, for 15 min to 24 h, preferably 30 min h to 12 h, most preferably 1 h to 5 h, such as 3-4 h. The compound can be converted into the respective acid salt by methods well known in the art. Typically the acid of choice is added to the amine. The acid can be any suitable organic or inorganic acid, preferably an inorganic acid such as HCl or an organic acid such as tartartic acid or its derivatives for example di-O-toluoyl tartaric acid.

When conducting the reaction step as described above, the obtained products are racemic and all substituents are stereochemically cis to one another. That is, the configuration on C2 and the C5 positions is always cis and the configuration on C4 is cis relative to C2 and C5. Preferably the compound of formula IV has the stereochemistry as shown below in formula IVA.

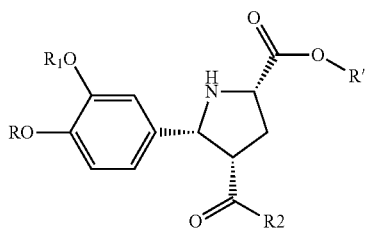

(IVA)

Chirality can be induced by carrying out the above-described cycloaddition reaction in the presence of a chiral catalyst formed by treatment with a suitable additive, see Husinec S and Savic, V., Tetrahedron Asymmetry 2005, 16, 2047-2061, incorporated herein by reference. Thus suitable additives include chiral phosphines and bisphosphines, in particular bisphosphines, such as compounds 25, 29, 30, 31, 32, 33, 39, 46, 47, 48 as disclosed in Husinec S and Savic, V., chiral oxazolines, such as compounds 56 and 57 as disclosed in Husinec S and Savic, V., ephedrine derived ligands, such as compound 15 as disclosed in Husinec S and Savic, V and other chiral ligands, such as compounds 20, 21, 22 and 23 as disclosed in Husinec S and Savic, V. Preferably the respective ligand is used together with the respective catalyst as reported in Husinec S and Savic, V. or as reported in Schreiber S. et al, J. Amer. Chem. Soc., 2003, 125, 10174, or as reported by Zhang X., et al J. Amer. Chem. Soc., 2002, 124, 13400, or as reported by Jorgensen K. A. et al, J. Org. Chem., 2003, 68, 2583, or as described by Pfalz. A. et al Synthesis, 2005, 1431. Ligands that are described in these references as preferred are also ligands of choice in the present application. As described by Schreiber S, et al or Zhang et al the choice of catalyst is also known to affect the stereochemistry of the newly formed substituent in the 2, 4 and 5 positions of the ring. Both optical isomers can thus be selectively prepared. The optical isomers can also be obtained by classical resolution techniques, for example fractional crystallisation of a suitable salt or by chromatographic separation of the optical isomers by employing chromatography on a chiral column.

As mentioned before, when conducting the cycloaddition reaction with or without a chiral additive, the stereochemistry of the substituent at C4 of the pyrrolidine ring is opposite to that required for SPP100. By employing compound V, in particular methyl vinyl ketone, in the cycloaddition process the substituents at C2 and C4 are differentiated (literature normally has both as different esters). This allows convenient selective manipulation of the C4 substituent.

Other options of inducing chirality include employing a chiral glycine ester, for example a L or D-menthylester which renders the process chiral and the compound of formula IV is obtained in enantiomeric excess. Enantioenrichment is then achieved by fractional crystallisation.

Another important embodiment of the invention relates to a compound of the formula IV as defined above, or a salt thereof. A compound of the formula IV may be used, inter alia, for the synthesis of pharmaceutically active substances, preferably renin inhibitors such as aliskiren, especially as described in the following.

In a preferred further embodiment of the invention, this synthesis comprises as a further step or as individual synthesis the manufacture of a compound of formula VI

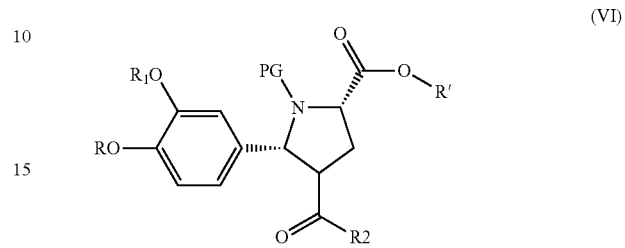

(VI)

wherein R, $R_1$ and R' are as defined for a compound of the formula III above, $R_2$ is as defined for a compound of the formula IV above and PG is an amino protecting group, or a salt thereof, said manufacture comprising (preferably consisting of) introducing an amino protecting group on the pyrrolidine nitrogen of a compound of formula IV, especially synthesized as in the preceding step. This process step as such, as well as a compound of the formula VI (and its preferred embodiments as described later), or a salt thereof, also form embodiments of the invention.

Preferably the compound of formula VI has the stereochemistry as shown below in formula VIA.

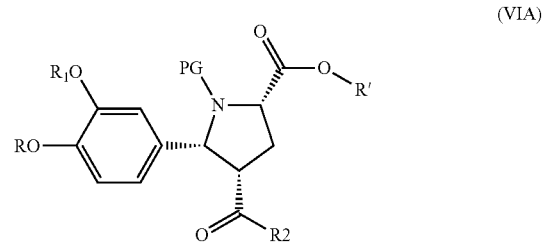

(VIA)

This conversion proceeds under standard conditions and as described e.g. in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974.

In particular when PG is an alkoxy carbonyl group so as to form a carbamate, the reaction is preferably conducted under basic or acidic conditions, more preferably basic conditions. Suitable bases include organic or inorganic bases, preferably organic bases, more preferably a nitrogen base, yet more preferably a tertiary nitrogen base. Examples of the tertiary nitrogen base include triethylamine, diisopropylethylamine, DBU, TMEDA and trimethylamine. The reaction can be conducted in any suitable solvent, preferably a polar solvent such as an ethyl acetate or a halogenated solvent, more preferably methylene chloride or ethyl acetate. The reaction time and the temperature are chosen so as to bring the reaction to completion at a minimum time without the production of unwanted side products. Typically the reaction can be conducted at 0° C. to reflux, preferably 0 to 40° C., more preferably 15-30° C., such as room temperature, for 10 min to 12 h, preferably 20 min to 6 h, most preferably 30 min to 4 h, such as 1 h.

Another important embodiment of the invention relates to a compound of the formula VI as defined above, or a salt thereof. A compound of the formula VI may be used, inter alia, for the synthesis of pharmaceutically active substances, preferably renin inhibitors such as aliskiren, especially as described in the following.

In a preferred further embodiment of the invention, this synthesis comprises as a further step or as individual synthesis the manufacture of a compound of formula VII

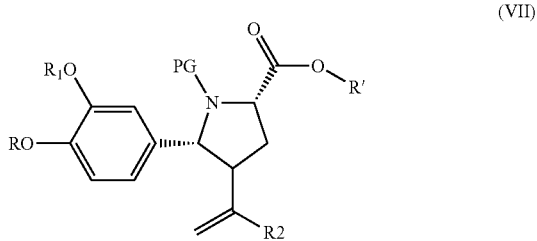

(VII)

wherein R, $R_1$ and R' are as defined for a compound of the formula III above, $R_2$ is as defined for a compound of the formula IV above and PG is an amino protecting group, or a salt thereof, said manufacture comprising (preferably consisting of) conversion of the carbonyl of a compound of the formula VI, especially synthesized as in the preceding step, to an olefin. This process step as such, as well as a compound of the formula VII (and its preferred embodiments as described later), or a salt thereof, also form embodiments of the invention.

The conversion can be effected by any method known to the person skilled in the art. Preferably the reaction is a Wittig or Wittig type reaction or a Peterson olefination or by reaction with the Petasis reagent. Typical reagents for the Wittig reaction are phosphorus ylides obtainable from the respective phosphonium salt and a base. The phosphonium salt is preferably obtainable from a phosphine, e.g. an aryl phosphine or an alkyl phosphine, and a methyl halide, such as MeBr. Triphenyl phosphine is the phosphine of choice. The ylide can also be prepared from phosphonates, phosphine oxides, phosphonic acid bisamides and alkyl phosphonothiates instead of phosphines. In this context phosphonates are preferred and the reaction is referred to as the Horner-Emmons reaction. The base used to prepare the ylides is preferably a strong base depending on the salt employed. Examples include sodium hydride, butyl lithium, lithium di-isopropyl amide, sodium amide, or a sodium alkoxide, preferably sodium hydride, butyl lithium or lithium di-isopropyl amide. Preferably the ylide is prepared in situ prior to addition of a compound of formula VI. The Wittig or Wittig type reaction takes place preferably in an inert solvent. More preferably in tetrahydrofuran or toluene. The reaction time and the temperature are chosen so as to bring the reaction to completion at a minimum time without the production of unwanted side products. Typically the reaction can be conducted at −78° C. to reflux,
preferably −30 to 30° C., more preferably −15 to 10° C., such as 0° C., 10 min h to 12 h, preferably 20 min to 6 h, most preferably 30 min to 4 h, such as 1 to 2 h.

The Peterson reaction can be carried out by standard methods, see for example Peterson D. J., J. Org. Chem. 1968, 33, 780. The use of the Petasis reagent can be exemplified by for example employing the methods found in Petsisi. N. A. et al J. Amer. Chem. Soc., 1990, 112, 6392, and Petasis N. A., et al Tetrahedron Letters, 1995, 36, 2393 and Payack J, F., Org. Process Research & dev. 2004, 8, 256.

Under the basic conditions of the Wittig reaction epimerization of the C4 substituent can be observed. Therefore when utilizing the preferred diastereomer resulting from formula IVA as shown above, the desired stereochemistry as shown in formula VIIA below and as required, e.g. for Aliskiren can be obtained:

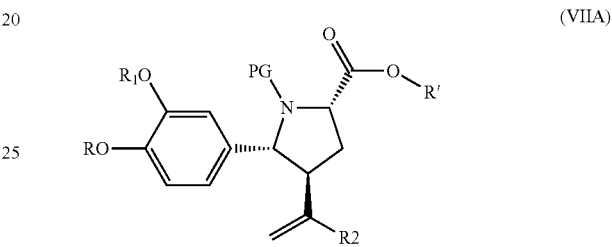

(VIIA)

Another important embodiment of the invention relates to a compound of the formula VI as defined above, or a salt thereof. A compound of the formula VII may be used, inter alia, for the synthesis of pharmaceutically active substances, preferably renin inhibitors such as aliskiren, especially as described in the following.

In a preferred further embodiment of the invention, this synthesis comprises as a further step or as individual synthesis the manufacture of a compound of formula VIII

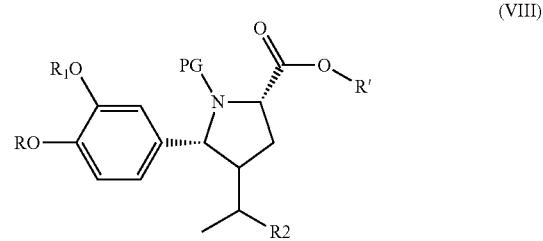

(VIII)

wherein R, $R_1$ and R' are as defined for a compound of the formula III above, $R_2$ is as defined for a compound of the formula IV above and PG is an amino protecting group, or a salt thereof, said manufacture comprising (preferably consisting on hydrogenation of the olefin of a compound of the formula VII, especially synthesized as in the preceding step. This process step as such, as well as a compound of the formula VIII (and its preferred embodiments as described later), or a salt thereof, also form embodiments of the invention.

Preferably the compound of formula VIII has the stereochemistry as shown below in formula VIIIA.

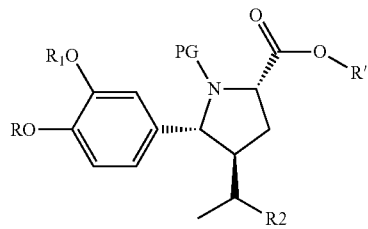

(VIIIA)

This reaction preferably takes place under conditions so as to keep the other functionalities on the molecule intact, in particular the amino protecting group PG. Hydrogenation typically takes place in the presence of a catalyst selected from a heterogeneous catalyst or a homogeneous catalyst, such as Wilkinson's catalyst, preferably a heterogeneous catalyst. Examples of the catalyst include Raney nickel, palladium/C, nickel boride, platinum metal or platinum metal oxide, rhodium, ruthenium and zinc oxide, more preferably Palladium/C, platinum metal or platinum metal oxide, most preferably palladium/C. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at atmospheric pressure. The hydrogenation takes place preferably in an inert solvent, more preferably in tetrahydrofuran or toluene. The reaction time and the temperature are chosen so as to bring the reaction to completion at a minimum time without the production of unwanted side products. Typically the reaction can be conducted at 0° C. to reflux, preferably 0 to 40° C., more preferably 15-30° C., such as room temperature, for 10 min h to 12 h, preferably 20 min to 6 h, most preferably 30 min to 4 h, such as 1 to 3 h.

Another important embodiment of the invention relates to a compound of the formula VIII as defined above, or a salt thereof. A compound of the formula VIII may be used, inter alia, for the synthesis of pharmaceutically active substances, preferably renin inhibitors such as aliskiren, especially as described in the following.

In a preferred further embodiment of the invention, this synthesis comprises as a further step or as individual synthesis the manufacture of a compound of formula IX

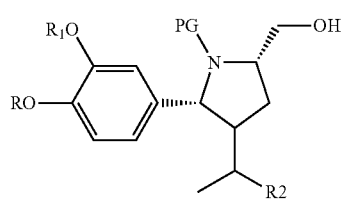

(IX)

wherein R and $R_1$ are as defined for a compound of the formula III above, $R_2$ is as defined for a compound of the formula IV above and PG is an amino protecting group, or a salt thereof, said manufacture comprising (preferably consisting of) reduction of the ester moiety of a compound of the formula VIII, especially synthesized as in the preceding step, to an alcohol. This process step as such, as well as a compound of the formula IX (and its preferred embodiments as described later), or a salt thereof, also form embodiments of the invention.

Preferably the compound of formula IX has the stereochemistry as shown below in formula IXA.

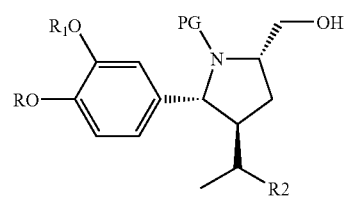

(IXA)

This reaction preferably takes place under conditions so as to keep the other functionalities on the molecule intact, in particular the amino protecting group PG. Such a reaction is well known to a person skilled in the art and is described e.g. in Methoden der organischen Chemie" (*Methods of Organic Chemistry*), Houben Weyl, 4th edition, Volume IV/c, Reduction I & II. Georg Thieme Verlag, Stuttgart 1974, The reduction typically takes place in the presence of a suitable reducing agent selected from $LiAlH_4$, Lithium trialkoxyaluminium hydrides, for example, lithium tri-tert-butyloxy aluminium hydride, DIBALH, Red-Al, lithium triethylborohydride, $BH_3$—$SMe_2$, $LiBH_4$, Trialkylammoniumborohydrides and $NaBH_4$. A preferred example of the reagent is $NaBH_4$ due to its selectivity.

The reduction takes place preferably in an inert solvent, more preferably in tetrahydrofuran or toluene. The reaction time and the temperature are chosen so as to bring the reaction to completion at a minimum time without the production of unwanted side products. Typically the reaction can be conducted at −78° C. to reflux, preferably −30 to 30° C., more preferably −15 to 10° C., such as 0° C., for 10 min h to 12 h, preferably 20 min to 6 h, most preferably 30 min to 4 h, such as 1 to 3 h.

A compound of the formula IX can then be further used in a number of ways in the synthesis of renin inhibitors such as aliskiren. Preferably, the compound is subjected to the steps as described in detail in GB application no. 0511686.8 as shown below.

Thus, a process for the synthesis of a renin inhibitor, such as aliskiren, comprises oxidizing a compound of the formula IX, especially synthesized as in the preceding steps, to an oxo compound of the formula X,

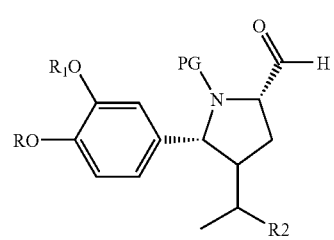

(X)

wherein R and $R_1$ are as defined for a compound of the formula III above, $R_2$ is as defined for a compound of the formula IV above and PG is an amino protecting group.

Preferably the compound of formula X has the stereochemistry as shown below in formula XA.

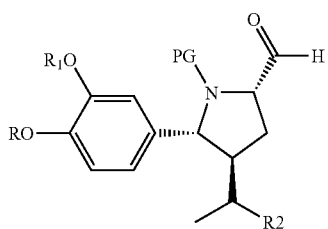

(XA)

The reaction especially takes place under customary conditions that allow for the oxidation of a hydroxy group to an oxo group and employing customary oxidizing reagents (oxidants). This reaction can make use of such oxidants that allow for the direct conversion from a compound of the formula IX of a corresponding aldehyde of the formula X, or a salt thereof, or it can be lead by first oxidizing to a carboxyl compound of the formula XI,

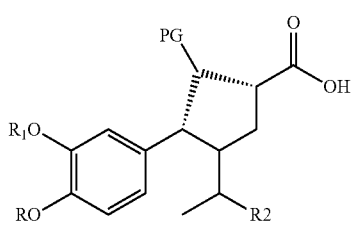

(XI)

wherein R and $R_1$ are as defined for a compound of the formula III above, $R_2$ is as defined for a compound of the formula IV above and PG is an amino protecting group, which can then be reduced with reducing agents to an aldehyde of the formula X. The direct reaction to an aldehyde of the formula X, can, for example, take place in the presence of an oxidant that allows for the oxidation of an alcohol to an aldehyde without undue formation of the acid of the formula XI, e.g. under Oppenauer conditions (e.g. using cyclohexanone, cinnamic aldehyde or anisaldehyde as oxidant in the presence of an aluminium alcoholate, such as aluminium-tert.-butoxyalcoholate), preferably with chromic acid, dichromate/sulphuric acid, pyridinium-chlorochromate, pyridinium dichromate, nitric acid, manganese dioxide or selenium dioxide or by catalytic dehydrogenation, or more preferably using oxidants useful under mild reaction conditions, such as TEMPO oxidation (TEMPO=2,2,6,6-tetramethylpiperidine-nitroxyl) with bleach, e.g. sodium sodium chloride or calcium hypochlorite, preferably in the presence of a bromide salt, e.g. potassium bromide, in an appropriate solvent, such as methylene chloride and/or water, or with diacetoxyiodobenzene in an appropriate solvent, e.g. methylene chloride, at temperatures e.g. from 0 to 50° C.; under Swern conditions, e.g. using dimethylsulfoxide in the presence of oxalyl chloride, e.g. at lowered temperatures, such as from −90 to 0° C., preferably in the presence of a tertiary nitrogen base, such as triethylamine; under Corey-Kim conditions, e.g. using dimethylsulfide in the presence of N-chloro-succinimide; using Moffat-Pfitzner conditions, e.g. oxidation with dimethylsulfoxide in the presence of dicyclohexyl-carbodiimide; Dess-Martin oxidation in the presence of Dess-Martin-periodinane (1,1,1-triacetoxy-1,1-dihydro-1,2-benziodoxol-3(1H)-one) in an appropriate solvent, such as methylene chloride, e.g. at temperatures from 0 to 50° C.; or using $SO_3$/pyridine complex in dimethylsulfoxide in the absence or presence of an appropriate solvent such as methylene chloride at temperatures e.g. from −30 to 30° C.; or with lower preference using catalytic dehydrogenation, e.g. in the presence of silver, copper, copper chromium oxide or zinc oxide. Where required, the stoichiometry of the oxidants is chosen appropriately to avoid over-oxidation.

The oxidation of a compound of the formula IX (or also an aldehyde compound of the formula X obtained preferably as described above) to a compound of the formula XI can, for example, take place with Jones reagent ($CrO_3$ in aqueous sulphuric acid/acetone), with manganese dioxide, with pyridinium dichromate or especially under Pinnick oxidation conditions, e.g. by oxidation with sodium chloride or calcium hypochlorite in the presence of a base, preferably an alkali-metal dihydrogenphosphate, e.g. sodium dihydrogenphosphate, in an appropriate solvent or solvent mixture, e.g. an alcohol, such as tert-butanol, 2-methyl-2-butene and/or water, at temperatures e.g. from 0 to 50° C. The reduction of an acid compound of the formula XI then can take place using reducing agents that allow for the selective reduction to an aldehyde of the formula X. The reducing agents can, for example, be selected from appropriate complex hydrides, such as $BH_3$—$SMe_2$, and the compound of the formula XI can also be used in a form with activated carboxyl group, e.g. as acid halogenide, active ester, (e.g. mixed) anhydride or by in situ activation, e.g. in an active form or by activation as described below for the coupling of a compound of the formula XI and a compound of the formula XIV which compound will be described later. For example, in the case of an acid chloride of a compound of the formula XI, the reduction to an aldehyde of the formula X can take place with LiAlH (tert-butoxy)$_3$ (lithium-tri(tert-butoxy)aluminiumhydride) in an appropriate solvent, e.g. 2-methoxyethyl ether (diglyme), or sodium borohydride or complexes thereof can be used. Alternatively, the reduction can take place by hydrogenation in the presence of partially poisoned hydrogenation catalysts, e.g. under Rosenmund reduction conditions using palladium/barium sulfate and hydrogen in an appropriate solvent, such as water, an alcohol, such as methanol or ethanol, dioxane, acetyl acetate or mixture of tow or more such solvents, at customary temperatures, e.g. from 0 to 80° C.

Alternatively the compound of formula X can be obtained by different approaches. One approach involves as a further step or as individual synthesis the manufacture of a compound of formula XII

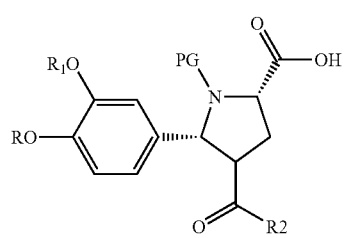

(XII)

wherein R and $R_1$ are as defined for a compound of the formula III above, $R_2$ is as defined for a compound of the formula IV above and PG is an amino protecting group, said manufacture comprising (preferably consisting of) hydrolysis of the ester moiety of a compound of the formula VI, especially synthesized as in the preceding step, to an acid.

The reaction is preferably conducted under basic or acidic conditions, more preferably basic conditions. Suitable bases include organic or inorganic bases, preferably inorganic bases, more preferably hydroxides or carbonates of alkali metals. Examples of preferred bases include LiOH, sodium hydroxide, potassium hydroxide, potassium carbonate. The reaction can be conducted in any suitable solvent, preferably an aqueous solvent system such as water/tetrahydrofuran, or aqueous alcohols for example methanol, ethanol water mixtures more preferably water/tetrahydrofuran. The reaction time and the temperature are chosen so as to bring the reaction to completion at a minimum time without the production of unwanted side products. Typically the reaction can be conducted at 0° C. to reflux, preferably 0 to 40° C., more preferably 15-30° C., such as room temperature, for 1 h to 48 h, preferably 6 h to 36 h, most preferably 12 h to 36 h, such as 24 h.

Under the conditions of the hydrolysis epimerization of the C4 substituent can be observed. Therefore when utilizing the preferred diastereomer resulting from formula IVA as shown above, the desired stereochemistry as shown in formula XIIA below and as required, e.g. for Aliskiren can be obtained:

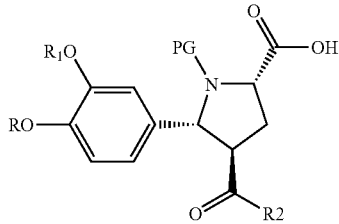

(XIIA)

A compound of the formula XIII may be used, inter alia, for the synthesis of pharmaceutically active substances, preferably renin inhibitors such as aliskiren, especially as described in the following.

In a preferred further embodiment of the invention, this synthesis comprises as a further step or as individual synthesis the manufacture of a compound of formula X as described above, said manufacture comprising (preferably consisting of) subjecting a compound of formula XIII to the steps of conversion of the ketone to an olefin according to method known in the art and as described e.g. in the above, and reduction of the carboxylic acid moiety to an aldehyde.

Another different approach to a compound of formula X involves as a further step or as individual synthesis the manufacture of a compound of formula XIII

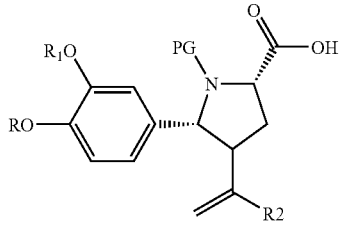

(XIII)

wherein R and $R_1$ are as defined for a compound of the formula III above, $R_2$ is as defined for a compound of the formula IV above and PG is an amino protecting group, said manufacture comprising (preferably consisting of) hydrolysis of the ester moiety of a compound of the formula VII especially synthesized as in the preceding step, to an acid.

Preferably the compound of formula XIII has the stereochemistry as shown below in formula XIIIA.

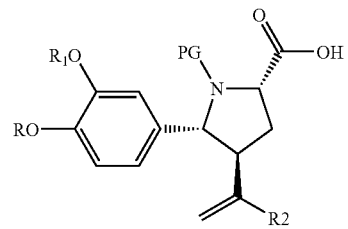

(XIIIA)

This conversion proceeds under standard conditions and as described e.g. in standard reference works.

The reaction is preferably conducted under basic or acidic conditions, more preferably basic conditions. Suitable bases include organic or inorganic bases, preferably inorganic bases. Examples of preferred base include LiOH, sodium hydroxide, potassium hydroxide, potassium carbonate. The reaction can be conducted in any suitable solvent, preferably an aqueous solvent system such as water/tetrahydrofuran, or aqueous alcohols for example methanol, ethanol water mixtures more preferably water/tetrahydrofuran. The reaction time and the temperature are chosen so as to bring the reaction to completion at a minimum time without the production of unwanted side products. Typically the reaction can be conducted at 0° C. to reflux, preferably 0 to 40° C., more preferably 15-30° C., such as room temperature, for 1 h to 48 h, preferably 6 h to 36 h, most preferably 12 h to 36 h, such as 24 h.

A compound of the formula XIII may be used, inter alia, for the synthesis of pharmaceutically active substances, preferably renin inhibitors such as aliskiren, especially as described in the following.

In a preferred further embodiment of the invention, this synthesis comprises as a further step or as individual synthesis the manufacture of a compound of formula X as described above, said manufacture comprising (preferably consisting of) hydrogenation of the olefin of a compound of the formula XIII, especially as synthesized as in the preceding step, followed by reduction to the aldehyde.

The hydrogenation reaction preferably takes place under conditions so as to keep the other functionalities on the molecule intact, in particular the amino protecting group PG. Hydrogenation typically takes place in the presence of a catalyst selected from a heterogeneous catalyst or a homogeneous catalyst, such as Wilkinson's catalyst, preferably a heterogeneous catalyst. Examples of the catalyst include Raney nickel, palladium/C, nickel boride, platinum metal or platinum metal oxide, rhodium, ruthenium and zinc oxide, more preferably Palladium/C, platinum metal or platinum metal oxide, most preferably palladium/C. The catalyst is preferably used in an amount of 1 to 20%, more preferably 5 to 10%. The reaction can be conducted at atmospheric or elevated pressure, such as a pressure of 2-10 bar, e.g. 5 bar, more preferably the reaction is conducted at atmospheric pressure. The hydrogenation takes place preferably in an inert solvent, more preferably in tetrahydrofuran or toluene. The reaction time and the temperature are chosen so as to bring the reaction to completion at a minimum time without the production of unwanted side products. Typically the reaction can be conducted at 0° C. to reflux, preferably 0 to 40° C., more preferably 15-30° C., such as room temperature, for 10 min h to 12 h, preferably 20 min to 6 h, most preferably 30 min to 4 h, such as 1 to 3 h.

A yet different approach to a compound of formula X involves as a further step or as individual synthesis the reduction of the ester moiety of a compound of the formula VIII, especially as synthesized as in the preceding step, to an aldehyde.

The different methods for obtaining compounds of formula X using any of the methods described above either alone or in combination are summarized in Scheme 1 below:

A compound of the formula X can then be further used in a number of ways in the synthesis of renin inhibitors such as aliskiren. Preferably, the compound is subjected to the steps as described in detail in GB application no. 0511686.8 as shown below. For sake of convenience the transformations are only shown for the case when $R_2$ is methyl to give an isopropyl substituent. Although this embodiment is preferred, the transformations can be carried out equally well with compounds as prepared above where $R_2$ has any other definition. In all of the compounds shown below the position of the

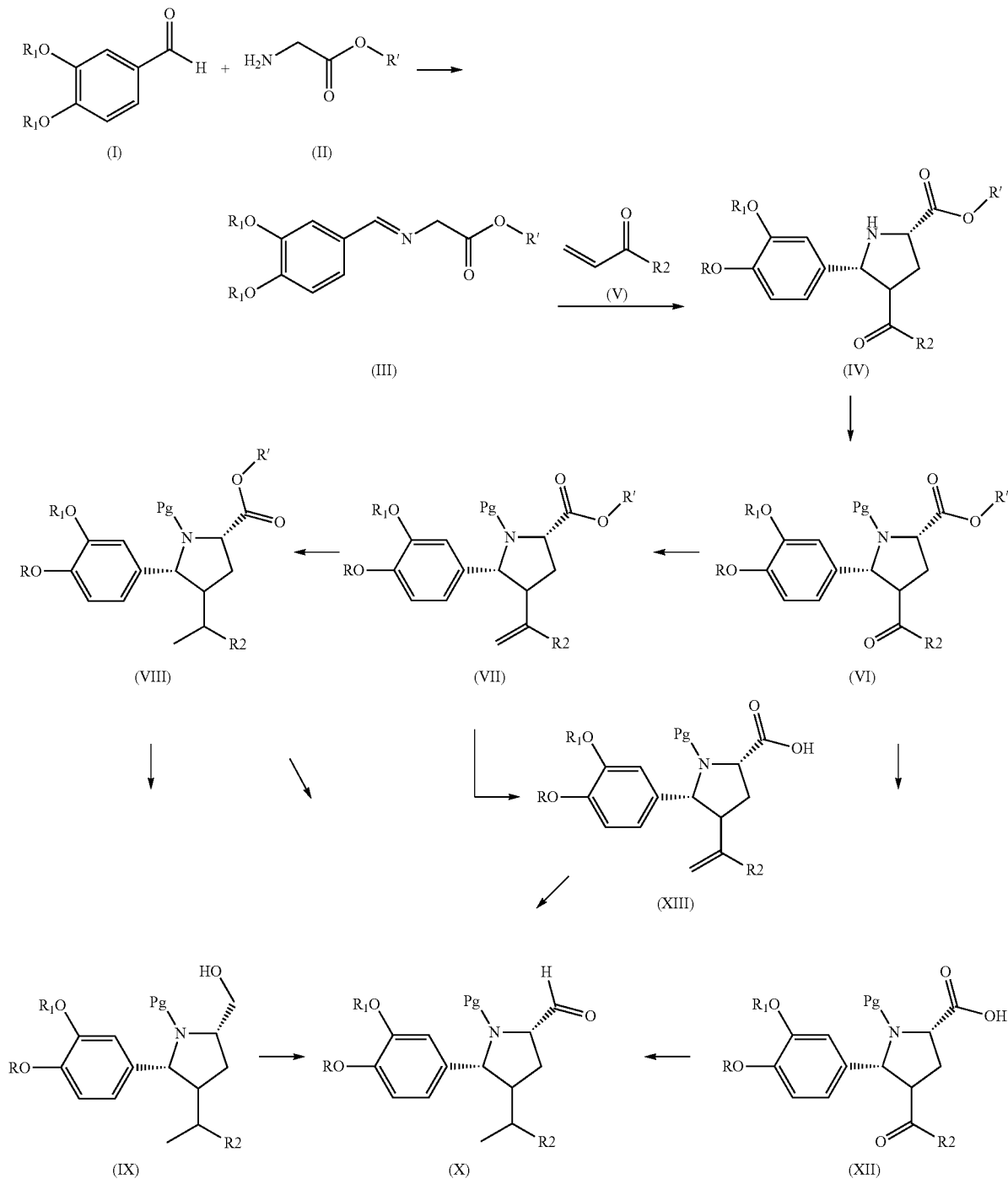

substituent bearing R₂ being methyl (i.e. resulting in an isopropyl substituent) has a defined stereochemistry, preferably the S-configuration.

Thus, a process for the synthesis of a renin inhibitor, such as aliskiren, further comprises reacting a compound of the formula X as just defined under Grignard or Grignard-like conditions with a reagent prepared by reaction of a compound of the formula XIV,

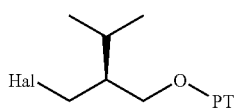
(XIV)

wherein Hal is halo, preferably chloro, bromo or iodo, and PT is a hydroxyl protecting group, with a metal, to give a compound of the formula XV,

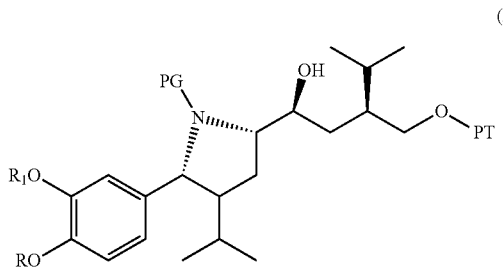
(XV)

wherein R, R₁ and PG are as defined under formula III and PT is a hydroxyl protecting group, preferably one that can be selectively removed without removal of the protecting group PG, e.g. 1-phenyl-$C_1$-$C_7$-alkyl, such as benzyl, or a salt thereof. The diastereoselectivity of this reaction is very high, e.g. larger than 99:1, that is, the other possible diastereoisomer is practically not observed. This shows a high advantage of the use of the pyrrolidine ring system for this conversion and thus also in the synthesis of renin inhibitors such as aliskiren.

The reaction preferably takes place with a metal reacting with the compound of the formula VI to give the corresponding metal compound, e.g. a lithium, sodium, iron, zinc, tin, indium, manganese, aluminium or copper metal compound, or MnX, (alkyl)₃MnLi—, or —CeX₂ wherein X is halogen such as Cl, I or Br, more preferably Br; or further a reagent obtainable with metal combinations, such as Mg/Fe, or still further with Lewis acids, such as BF₃.diethyl ether complex or MgBr₂, or the like, to give a Grignard-like reagent for Grignard-like reaction, or with magnesium giving the corresponding Grignard reagent with magnesium (Mg) as the metal for Grignard reaction, in an appropriate solvent, e.g. an ether, such as a cyclic ether, e.g. tetrahydrofuran, an alkyl ether, e.g. diethyl ether, tert-butylmethyl ether, a hydrocarbon, such as toluene, or a halogenated hydrocarbon, e.g. methylene chloride, at temperatures e.g. in the range from 0 to 70° C. Grignard or Grignard-like reagents or organo lithium compounds are preferred, and Grignard or Grignard-like reagents are particularly preferred.

A process for the synthesis of a renin inhibitor, such as aliskiren, further comprises deprotecting a compound of the formula XV as just defined by removal of the hydroxy protecting group PT, for example in the case of a protecting group that can be removed by hydrogenation such as 1-phenyl-$C_1$-$C_7$-alkyl, e.g. benzyl, by catalytic hydrogenation, to give a compound of the formula XVI,

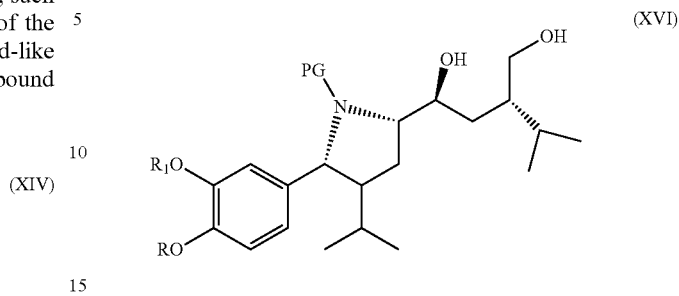
(XVI)

wherein R, R₁ and PG are as defined under formula III above, or a salt thereof. The deprotection takes place under standard conditions, e.g. in the case of removal of the protecting group by hydrogenation with hydrogen in the presence of a catalyst, such as a noble metal catalyst, e.g. palladium, which may be present on a carrier, such as charcoal, in an appropriate solvent, such as an alcohol, e.g. methanol or ethanol, or non-alcoholic solvents such as (but not restricted to) toluene or ethyl acetate, at appropriate temperatures, e.g. in the range from 0 to 50° C.

A process for the synthesis of a renin inhibitor, such as aliskiren, further comprises oxidizing a compound of the formula XVI at the primary hydroxy group to an aldehyde compound of the formula XVII,

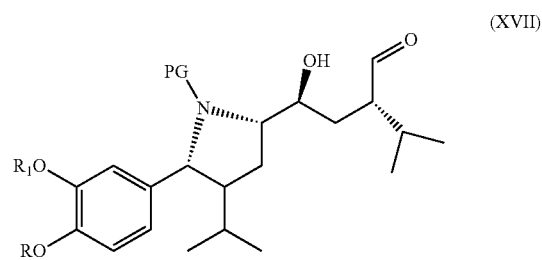
(XVII)

wherein R, R₁ and PG are as defined under formula III above, or a salt thereof, which then cyclizes spontaneously to produce a lactol of the formula XVIII,

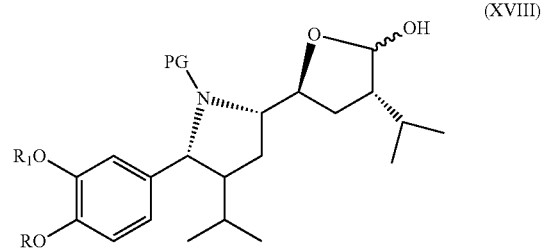
(XVIII)

which, either in the same reaction mixture (in situ) or after isolation and in a separate process step, is then oxidized to a lactone of the formula XIX, (XIX)

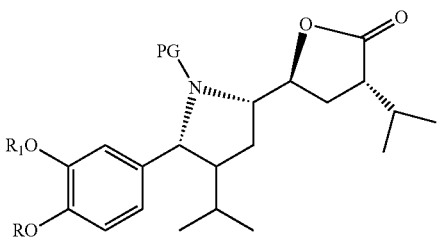

wherein in formula XVIII and XIX R, $R_1$ and PG are as defined for a compound of the formula III above. The oxidation of a compound of the formula XVI resulting in the lactol of the formula XVIII preferably takes place under the conditions mentioned to be preferred for oxidation of a compound of the formula IX to an aldehyde of the formula X, e.g. with $SO_3$/pyridine in the presence of dimethylsulphoxide in an appropriate solvent, such as methylene chloride, preferably in the presence of a tertiary nitrogen base, such as triethylamine, e.g. at temperatures from −30 to 50° C. The subsequent oxidation to the compound of the formula XIX can take place under the same reaction conditions employing an excess of some of the reagents mentioned above or it can be isolated and oxidized separately with further reagents, e.g. those mentioned above, more preferably using TEMPO/diacetoxyiodo benzene.

Alternatively, it can also be oxidized at the primary alcohol without effecting the secondary alcohol to compound XIX with the reagent TPAP (Tetra-N-propylammonium perruthenate, e.g. according to lit. ref., S. Ley et al. Synthesis, 639 (1994). This method is particularly preferred.

In a further embodiment, a process for the synthesis of a renin inhibitor, such as aliskiren, further comprises reacting a compound of the formula XIX as just defined, or a salt thereof, with an amine of the formula XX, (XX)

$H_2N\diagup\diagdown NH_2$
$\phantom{H_2N\diagup}O$ (wherein the amido nitrogen can also be protected if desired and the protecting group then be removed in the corresponding protected compound of the formula XXI), or a salt thereof, obtaining a compound of the formula XXI, (XXI)

[structure]

wherein R, $R_1$ and PG are as defined for a compound of the formula III, or a salt thereof.

The reaction preferably takes place under standard conditions for the formation of an amide from a lactone, e.g. in an appropriate solvent or solvent mixture, e.g. in an ether, such as tert-butylmethyl ether, preferably in the presence of a bifunctional catalyst with a weak acidic and a weak basic group, e.g. 2-hydroxypyridine or proline, in the presence of an appropriate base, e.g. a tertiary nitrogen base, such as triethylamine, at appropriate temperatures e.g. in the range from 0° C. to the reflux temperature of the reaction mixture, e.g. from 0 to 85° C.

In a further embodiment a process for the synthesis of a renin inhibitor, such as aliskiren, further comprises opening the ring in a compound of the formula XXI by reductive ring opening to a compound of the formula XXII,

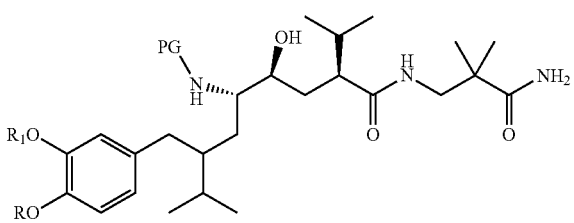

(XXII)

wherein R, $R_1$ and PG are as defined for a compound of the formula III, or a salt thereof.

The reductive ring opening preferably takes place under conditions employing appropriate metals as reductants, e.g. under conditions comparable to those of a Birch reduction with alkali metals and liquid ammonia, e.g. with sodium or lithium in the presence of liquid ammonia ($NH_3$) in the presence or absence of an appropriate further solvent or solvent mixture, such as an ether, e.g. tetrahydrofurane, and/or an alcohol, e.g. ethanol, at lower temperatures, e.g. from −90 to −20° C., e.g. at about −78° C. Alternative reductions methods are possible, e.g. reduction with calcium in tert-butanol, other reduction methods with calcium, lithium-di-tert-butylbiphenylide, magnesium in anthracene, or the like, which do not require the use of liquid ammonia and low temperatures (<−20° C.).

In a further embodiment, a process for the synthesis of a renin inhibitor, such as aliskiren, further comprises deprotecting a compound of the formula XXII to give the corresponding compound of the formula XXIII,

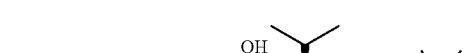

(XXIII)

which is pharmaceutically active, especially as a renin inhibitor, wherein R and $R_1$ are as defined for a compound of the formula III, or a salt thereof; and, if desired, converting an obtainable free compound of the formula XXIII into a salt or an obtainable salt into the free compound of the formula XXIII or a different salt thereof. For example, if PG is (what is preferred) a $C_1$-$C_7$-alkoxycarbonyl group, such as tert-butoxycarbonyl, the removal can take place under customary conditions, e.g. in the presence of an acid, such as hydrohalic acid, in an appropriate solvent, such as dioxane, e.g. at temperatures from 0 to 50° C., for example at room temperature.

In an aspect the process for the manufacture of a compound of the formula XXIII, or a salt thereof, comprises first opening the ring in a compound of the formula XXI as described above by reducing it selectively to a compound of the formula XXII as described above, or a salt thereof, and then deprotecting a compound of the formula XXII to give the corresponding compound of the formula XXIII, or a salt thereof, and, if desired, converting an obtainable free compound of the formula XXIII into a salt or an obtainable salt into the free compound of the formula XIII or a different salt thereof.

Alternatively, as a second embodiment, a process for the synthesis of a renin inhibitor, such as aliskiren, comprises reacting a compound of the formula XI (which can be obtained as described above or by first oxidizing a compound of the formula IX, this reaction can make use of such oxidants that lead to a corresponding aldehyde of the formula V, or a salt thereof, and then oxidizing the aldehyde of the formula X further to the carbonic acid of the formula XI, or a salt thereof, e.g. by reactions analogous to those described above) as described above, or a salt thereof (obtainable preferably as described above where the synthesis of a compound of the formula XI is first described) wherein R, $R_1$ and PG are as defined above for a compound of the formula III, or a salt thereof, with a reagent capable of activating the carboxyl group, especially capable of transforming it into an acid halide, a mixed acid anhydride or a carbonyl imidazolide, and then reacting it with a metallo-organic derivative of a compound of the formula XIV as defined above, especially a zinc or magnesium derivative, to a compound of the formula XXIV,

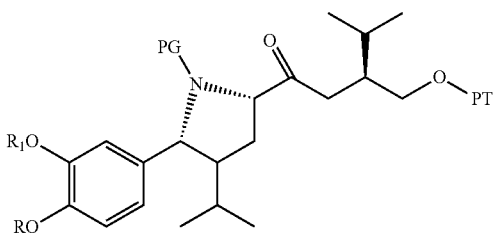

(XXIV)

wherein R, $R_1$ and PG are as defined for a compound of the formula III and PT is as defined for a compound of the formula XIV, or a salt thereof.

The activating of the carboxyl group in a compound of the formula XI to form a reactive derivative thereof preferably takes place under customary condensation conditions, where among the possible reactive derivatives of an acid of the formula XI reactive esters (such as the hydroxybenzotriazole (HOBT), pentafluorophenyl, 4-nitrophenyl or N-hydroxysuccinimide ester), imidazolide, acid halogenides (such as the acid chloride or bromide) or reactive anhydrides (such as mixed anhydrides with lower alkanoic acids or symmetric anhydrides) are preferred. Reactive carbonic acid derivatives can also be formed in situ. The reaction is carried out by dissolving the compounds of formula XI in a suitable solvent, for example a halogenated hydrocarbon, such as methylene chloride, N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and, if the reactive derivative of the acid of the formula II is formed in situ, a suitable coupling agent that forms a preferred reactive derivative of the carbonic acid of formula XI in situ, for example dicyclohexylcarbodiimide/1-hydroxybenzotriazole (DCC/HOBT); bis(2-oxo-3-oxazolidinyl)-phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. The reaction mixture is preferably stirred at a temperature of between approximately −20 and 50° C., especially between 0° C. and 30° C., e.g. at room temperature. The reaction is preferably carried out under an inert gas, e.g. nitrogen or argon.

The subsequent reaction with a metallo-organic derivative of a compound of the formula XIV, especially a zinc or magnesium derivative, or further a manganese, aluminium or copper derivative, then preferably takes place under customary conditions, e.g. analogous to the Grignard or Grignard-like conditions mentioned above for the reaction of a compound of the formula XIV with an aldehyde of the formula X.

In a further embodiment, a process for the synthesis of a renin inhibitor, such as aliskiren, comprises reducing a compound of the formula XXIV under stereoselective conditions and deprotecting the resulting compound under removal of the hydroxy protecting group PT to give a compound of the formula XVI as described above, or a salt thereof.

The reduction under stereoselective conditions preferably takes place in the presence of a stereoselective reductant, such as $LiAlH(O\text{-tert-butyl})_3$, $LiBH(sec\text{-butyl})_3$ (Selectride®), potassium selectride, or borohydride/oxaazaborolidine (("CBS-catalysts" originally based on the work of Corey, Bakshi and Shibata, synthesizable in situ from an amino alcohol and borane), or by stereoselective hydrogenation, e.g. in the presence of catalysts such as $[Ru_2Cl_4((S\text{- or }R\text{-})BI\text{-}NAP)]NEt_3$; the reactions take place under customary conditions, e.g. in appropriate solvents, such as tetrahydrofuran, methanol, ethanol, or mixtures of two or more such solvents, e.g. at temperatures from −80 to 50° C. (see, for example, Rueger et al., Tetrahedron Letters, 2000, 41, 10085.)

The deprotection then takes place under standard conditions, e.g. if PT is a protecting group that can be removed by hydrogenation such as 1-phenyl-$C_1$-$C_7$-alkyl, e.g. benzyl, by catalytic hydrogenation, for example under conditions analogous to those mentioned above for deprotection of a compound of the formula XV.

A compound of the formula XVI can be further reacted to a compound of the formula XVIII, or a salt thereof, as described above, which then can be further reacted via the reaction steps shown above to yield a compound of the formula XXIII, or a salt thereof.

Alternatively, a compound of the formula XVI as defined above, or a salt thereof, obtainable or preferably obtained either according to the first or the second embodiment of the invention, can be further reacted to a compound of the formula XXV,

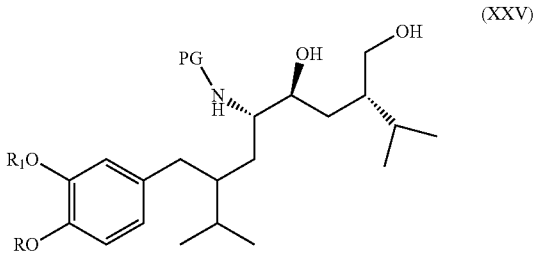

(XXV)

wherein R, R$_1$ and PG are as defined for a compound of the formula III, or a salt thereof, by reductive ring opening of the pyrrolidine ring. The reductive ring opening preferably takes place under conditions as those mentioned above for the ring opening in a compound of the formula XXI.

A compound of the formula XXV can then be oxidized in a further embodiment of said first or second embodiment in a process for the synthesis of a renin inhibitor, such as aliskiren, (comparably as a compound of the formula XVI via an aldehyde with opened pyrrolidine ring analogous to a compound of the formula XVII, preferably under conditions as described for that reaction) to a lactol of the formula XXVI,

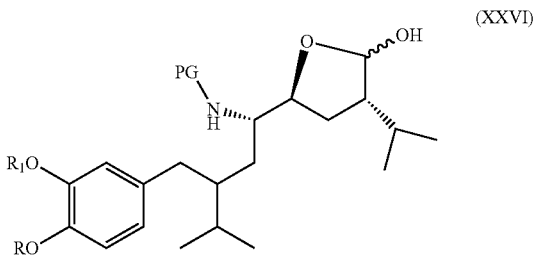

(XXVI)

wherein R, R$_1$ and PG are as defined for a compound of the formula III, or a salt thereof, which, either in the same reaction mixture (in situ) or after isolation, is then oxidized to a lactone of the formula XXVII

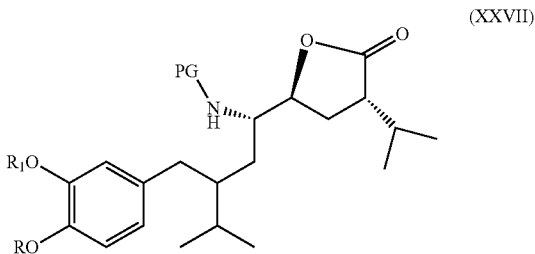

(XXVII)

wherein R, R$_1$ and PG are as defined for a compound of the formula III, or a salt thereof (where this reaction as such is also an embodiment of the present invention), the reaction preferably taking place under conditions analogous to those described above for oxidation a compound of the formula XVII to a compound of the formula XIX.

A compound of the formula XXVI can then, in a further embodiment of said first or second embodiment in a process for the synthesis of a renin inhibitor, such as aliskiren, be reacted with a compound of the formula XX defined above (if in protected form with subsequent deprotection of the amide nitrogen), preferably under analogous reaction conditions as described there, to a compound of the formula XXII as described above, or a salt thereof. The latter can then be deprotected as described above to give the final product of the formula XXIII described above, or a salt thereof.

In a third embodiment, a process for the synthesis of a renin inhibitor, such as aliskiren, comprises reacting a compound of the formula XV, or a salt thereof, as defined above (obtainable according to the first or second embodiment) by reductive ring opening to a compound of the formula XXVIII,

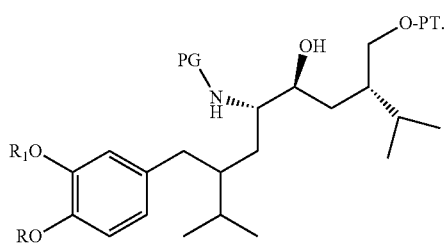

wherein R, R$_1$ and PG are as defined for a compound of the formula III and PT is a hydroxy protecting group, or a salt thereof, wherein PG=benzyloxycarbonyl and PT is benzyl or wherein PG is hydrogen and PT is benzyl are preferred. The reductive ring opening preferably takes place under conditions as those mentioned above for the ring opening in a compound of the formula XXI. A compound of the formula XXVIII, or a salt thereof, can then be reacted in analogy to a compound of the formula XXI above by removal of the protecting group to give a compound of the formula XXV as described above, or a salt thereof, which can then be further transformed e.g. via compounds XXVI and XXVII and XXII and preferably under analogous reaction conditions, or in each case a salt thereof, to a compound of the formula XXIII as defined above, or a salt thereof.

In a fourth embodiment, a process for the synthesis of a renin inhibitor, such as aliskiren, comprises reacting a compound of the formula XVIII, or a salt thereof, as defined above, by reductive ring opening to a compound of the formula XI as shown above, or a salt thereof, which reaction as such is also an embodiment of the invention. The reductive ring opening preferably takes place under conditions as those mentioned above for the ring opening in a compound of the formula XXI.

In a further embodiment of said fourth embodiment, a process for the synthesis of a renin inhibitor, such as aliskiren, comprises oxidising a compound of the formula XXVI, or a salt thereof, to give a lactone compound of the formula XXVIII, or a salt thereof, as described above (preferably under reaction conditions analogous to those for oxidation of a compound of the formula XVIII to a compound of the formula XIX as given above) which, in yet a further embodiment of said fourth embodiment of the invention, can then be reacted with a compound of the formula XIII, or a salt thereof, as described above, preferably under reaction conditions analogous to those described for reaction of a compound of the formula XI with a compound of the formula XX, to give a compound of the formula XXII as described above, or a salt thereof, which can then, in a further embodiment of said fourth embodiment, be deprotected into a compound of the formula XXIII, or a salt thereof, as described above, preferably under analogous conditions as described above for the deprotection of a compound of the formula XXII.

In a fifth embodiment, a process for the synthesis of a renin inhibitor, such as aliskiren, comprises reacting a compound of the formula XIX as described above, or a salt thereof, by reductive ring opening to give a compound of the formula XXVII, or a salt thereof, as described above. The reductive ring opening preferably takes place under conditions as those mentioned above for the ring opening in a compound of the formula XXI.

In a further embodiment of said fifth embodiment, a process for the synthesis of a renin inhibitor, such as aliskiren, comprises reacting a compound of the formula XXVII, or a salt thereof, with a compound of the formula XX, or a salt thereof, as described above, preferably under reaction conditions analogous to those mentioned above for reaction of a compound of the formula XIX with a compound of the formula XX, to give a compound of the formula XXII as described above, or a salt thereof, which can then, in a further embodiment of said fifth embodiment of the invention, be deprotected into a compound of the formula XXIII, or a salt thereof, as described above, preferably under reaction conditions analogous to those described above for deprotection of a compound of the formula XXII.

In a sixth embodiment, a process for the synthesis of a renin inhibitor, such as aliskiren, comprises reacting a compound of the formula X as described above, or a salt thereof, with a compound of the formula XXIX,

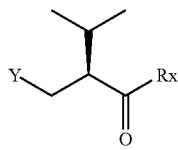

(XXIX)

wherein Y is $Ph_3P^+$ or $(AlkO)_2P(O)$ wherein Alk is preferably alkyl, e.g. $C_1$-$C_7$-alkyl, (both of which may also be prepared in situ, respectively) and Rx is hydroxy, protected hydroxy, amino or $NH-CH_2C(CH_3)_2-CONH_2$, resulting in a compound of the formula XXX,

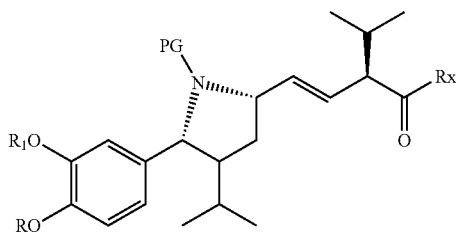

(XXX)

wherein R, $R_1$ and PG are as defined for a compound of the formula III and Rx is as defined for a compound of the formula XXIX; or a salt thereof. Here the reaction can take place in the presence of a suitable base, for example, sodium hydride, butyllithium, hexyllithium, cyclohexyllithium or lithium diisopropylamide, in appropriate solvents, such as ethers, e.g. tetrahydrofuran, hydrocarbons, e.g. toluene, or halogenated hydrocarbons, e.g. methylene chloride or mixtures of two or more such solvents, for example at temperatures between −78° C. and 100° C.

In a further embodiment of said sixth embodiment, a process for the synthesis of a renin inhibitor, such as aliskiren, comprises reacting a compound of the formula XXX, or a salt thereof, under reductive opening of the pyrrolidine ring and formation of an aziridino ring in formula XXX to give a compound of the formula XXXI,

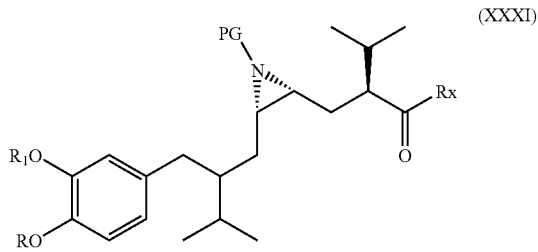

(XXXI)

wherein R, $R_1$ and PG are as defined for a compound of the formula III and Rx is as defined for a compound of the formula XXIX, or a salt thereof. The reductive ring opening preferably takes place under conditions as those mentioned above for the ring opening in a compound of the formula XXI.

In a further embodiment of said sixth embodiment, a process for the synthesis of a renin inhibitor, such as aliskiren, comprises reacting a compound of the formula XXXI, or a salt thereof, under ring opening to give a compound of the formula XXVII, or a salt thereof, if Rx in the compound of the formula is OH (or if it is protected hydroxy and the hydroxy protecting group is first removed to give OH). The ring opening reaction can, for example, take place under acidic or basic conditions, preferably in the presence of appropriate solvents, for example alcohols, such as ethanol or methanol, ethers, such as tetrahydrofuran, hydrocarbons, such as toluene, or halogenated hydrocarbons, such as methylene chloride, for example at temperatures between 0° C. and the reflux temperature of the respective reaction mixture. A compound of the formula XXVII, or a salt thereof, can then, in a further preferred embodiment of the sixth embodiment, be converted into a compound of the formula XXII as described above, or a salt thereof, by reacting it with a compound of the formula XX as defined above to a compound of the formula XXII as defined above, preferably under reaction conditions analogous to those mentioned above; which, in a further preferred embodiment of the sixth embodiment, can then be deprotected to a compound of the formula XXIII, or a salt thereof, preferably under conditions analogous to those described above for deprotection of a compound of the formula XXII.

In yet a further embodiment of said sixth embodiment, a process for the synthesis of a renin inhibitor, such as aliskiren, comprises reacting a compound of the formula XXXI, or a salt thereof, wherein Rx is $NH-CH_2C(CH_3)_2-CONH_2$, under ring opening (with conditions preferably analogous to those described in the preceding paragraph) to give a compound of the formula XXII, or a salt thereof. The latter can then, in a further preferred embodiment of this version of the sixth embodiment, be deprotected to a compound of the formula XXIII, or a salt thereof, preferably under conditions analogous to those described above for deprotection of a compound of the formula XXII.

All these different synthesis routes show that by providing the compound of the formula X in a more efficient manner, this central intermediate is useful to obtain renin inhibitors in a number of possible synthesis routes especially for the synthesis of renin inhibitors such as aliskiren.

Listed below are definitions of various terms used to describe the novel intermediates and synthesis steps of the present invention. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

Halo or halogen is preferably fluoro, chloro, bromo or iodo, most preferably fluoro, chloro or bromo; where halo is mentioned, this can mean that one or more (e.g. up to three) halogen atoms are present, e.g. in halo-$C_1$-$C_7$-alkyl, such as trifluoromethyl, 2,2-difluoroethyl or 2,2,2-trifluoroethyl.

Alkyl preferably has up to 20 carbon atom and is more preferably $C_1$-$C_7$-alkyl. Alkyl is straight-chained or branched (one or, if desired and possible, more times). Very preferred is methyl.

Alkoxyalkyl is alkyl (which is preferably as just defined) that is substituted at a carbon, preferably at a terminal carbon (in ω-position), with an alkyloxy (=alkoxy) group wherein alkyl is as defined above, preferably $C_1$-$C_7$-alkoxy. As alkoxyalkyl, 3-methoxypropyl is especially preferred.

Protecting groups may be present (see also under "General Process Conditions") and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. Preferably, if two or more protecting groups are present in one intermediate mentioned herein, they are chosen so that, if one of the groups needs to be removed, this can be done selectively, e.g. using two or more different protecting groups that are cleavable under different conditions, e.g. one class by mild hydrolysis, the other by hydrolysis under harder conditions, one class by hydrolysis in the presence of an acid, the other by hydrolysis in the presence of a base, or one class by reductive cleavage (e.g. by catalytic hydrogenation), the other by hydrolysis, or the like.

As hydroxyl protecting group, any group that is appropriate for reversible protection of hydroxy groups is possible, e.g. those mentioned in the standard textbooks under "General Process Conditions". A hydroxyl protecting group may, just to mention a few examples, be selected from a group comprising (especially consisting of) a silyl protecting group, especially diaryl-lower alkyl-silyl, such as diphenyl-tert-butylsilyl, or more preferably tri-lower alkylsilyl, such as tert-butyldimethylsilyl or trimethylsilyl; an acyl group, e.g. lower alkanoyl, such as acetyl; benzoyl; lower alkoxycarbonyl, such as tert-butoxycarbonyl (Boc), or phenyl-lower alkoxycarbonyl, such as benzyloxycarbonyl; tetrahydropyranyl; unsubstituted or substituted 1-phenyl-lower alkyl, such as benzyl or p-methoxybenzyl, and methoxymethyl. Boc (selectively removable by hydrolysis) and benzyl (selectively removable by hydrogenation) are especially preferred.

As amino protecting group, any group that is appropriate for reversible protection of hydroxy groups is possible, e.g. those mentioned in the standard textbooks under "General Process Conditions". An amino protecting group may, just to mention a few examples, be selected from a group comprising (especially consisting of) acyl (especially the residue of an organic carbonic acid bound via its carbonyl group or an organic sulfonic acid bound via its sulfonyl group), arylmethyl, etherified mercapto, 2-acyl-lower alk-1-enyl, silyl or N-lower alkylpyrrolidinylidene. Preferred amino-protecting groups are lower alkoxycarbonyl, especially tert-butoxycarbonyl (Boc), phenyl-lower alkoxycarbonyl, such as benzyloxycarbonyl, fluorenyl-lower alkoxycarbonyl, such as fluorenylmethoxycarbonyl, 2-lower alkanoyl-lower alk-1-en-2-yl and lower alkoxycarbonyl-lower alk-1-en-2-yl, with most preference being given to isobutyryl, benzoyl, phenoxyacetyl, 4-tert-butylphenoxyacetyl, N,N-dimethylformamidinyl, N-methylpyrrolidin-2-ylidene or especially tert-butoxycarbonyl.

A group X other than hydroxy or hydrogen is preferably a leaving group, e.g. halo, such as chloro, bromo or iodo, or the acyloxy moiety derived from an organic sulfonic acid, such as a alkanesulfonyloxy, especially $C_1$-$C_7$-alkanesulfonyloxy, e.g. methanesulfonyloxy, haloalkanesulfonyloxy, especially halo-$C_1$-$C_7$-alkanesulfonyloxy, such as trifluoromethanesulfonyloxy, or unsubstituted or substituted arylsulfonyloxy, such as toluolsulfonyloxy (tosyloxy).

Unsubstituted or substituted aryl is preferably a mono- or polycyclic, especially monocyclic, bicyclic or tricyclic aryl moiety with 6 to 22 carbon atoms, especially phenyl (very preferred), naphthyl (very preferred), indenyl, fluorenyl, acenapthylenyl, phenylenyl or phenanthryl, and is unsubstituted or substituted by one or more, especially one to three, moieties, preferably independently selected from the group consisting of $C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycarbonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfo, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro.

Salts are especially the pharmaceutically acceptable salts of compounds of formula XXIII or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds of formula XXIII or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethanesulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula XV or any of the intermediates mentioned herein may also form internal salts.

For isolation or purification purposes of compounds of the formula XXIII or in general for any of the intermediates mentioned herein it is also possible to use pharmaceutically unacceptable salts, for example picrates or perchlorates. For therapeutic use, only pharmaceutically acceptable salts or free compounds of the formula XXIII are employed (where applicable comprised in pharmaceutical preparations), and these are therefore preferred at least in the case of compounds of the formula XXIII.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula XXIII, is to be understood as referring also to one or more salts thereof or a mixture of a corresponding free compound, intermediate or starting material and one or more salts thereof, each of which is intended to include also any solvate, metabolic precursor such as ester or amide of the compound of formula XXIII, or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

Starting materials are especially the compounds of the formula I, II, and/or V mentioned herein, intermediates are especially compounds of the formula III, IV, VI, VII, VIII, IX, X, XI, XII and/or XIII.

The invention relates to methods of synthesis of the intermediates of the formula III, IV, VI, VII, VIII, IX, X, XI, XII and/or XIII mentioned above from their respective precursors as mentioned above. The invention relates also to methods of synthesis of the intermediates of the formula III, IV, VI, VII, VIII, IX, X, XI, XII and/or XIII mentioned above from their respective precursors as mentioned above, including methods with the single steps of a sequence leading to a compound of the formula XXIII, more than one or all steps of said synthesis and/or pharmaceutically active substances, especially renin inhibitors, most preferably aliskiren, including methods with the single steps of a sequence leading to a compound of the formula XXIII, more than one or all steps of said synthesis and/or pharmaceutically active substances, and/or their use in the synthesis of pharmaceutically active compounds, such as renin inhibitors, especially aliskiren.

In the following, the definitions of the substituents of the compounds described therein are provided including preferred embodiments. Each of the definition for one substituent, in particular a preferred definition, can be combined with any definition for the other substituents, in particular their preferred definitions.

R is hydrogen, alkyl or alkoxyalkyl, preferably alkyl, more preferably $C_1$-$C_7$-alkyl, especially methyl.

$R_1$ is hydrogen, alkyl or alkoxyalkyl; preferably alkoxyalkyl, more preferably $C_1$-$C_7$-alkoxy-$C_1$-$C_c$-alkyl, especially 3-methoxypropyl.

$R_2$ is alkyl, preferably $C_1$-$C_7$-alkyl, more preferably $C_1$-$C_3$-alkyl, especially methyl. Alternatively $R_2$ is preferably a chiral alkyl, such as D or L-menthyl.

R' is alkyl or aralkyl, preferably $C_1$-$C_7$-alkyl $C_1$-$C_3$-alkyl phenyl, more preferably $C_1$-$C_4$-alkyl or benzyl, especially ethyl.

General Process Conditions

The following, in accordance with the knowledge of a person skilled in the art about possible limitations in the case of single reactions, applies in general to all processes mentioned hereinbefore and hereinafter, while reaction conditions specifically mentioned above or below, in particular in the examples, are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula XXIII is designated a "protecting group", unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage). Different protecting groups can be selected so that they can be removed selectively at different steps while other protecting groups remain intact. The corresponding alternatives can be selected readily by the person skilled in the art from those given in the standard reference works mentioned above or the description or the Examples given herein.

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H⁺ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning. Where required or desired, water-free or absolute solvents can be used.

Where required, the working-up of reaction mixtures, especially in order to isolate desired compounds or intermediates, follows customary procedures and steps, e.g. selected from the group comprising but not limited to extraction, neutralization, crystallization, chromatography, evaporation, drying, filtration, centrifugation and the like.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula XV scribed as being preferred. Special preference is given to reaction conditions that are identical or analogous to those mentioned in the Examples. The invention relates also to novel starting compounds and intermediates described herein, especially those leading to compounds mentioned as preferred herein.

The invention especially relates to any of the methods described hereinbefore and hereinafter that leads to aliskiren, or a pharmaceutically acceptable salt thereof.

The following Examples serve to illustrate the invention without limiting the scope thereof, while they on the other hand represent preferred embodiments of the reaction steps, intermediates and/or the process of manufacture of aliskiren, or salts thereof.

Where mentioned in the Examples, "boc" stands for tert-butoxycarbonyl.

EXAMPLES

The following amino acid esters are new compounds

Amino acetic acid-4-nitrobenzyl ester hydrochloride: To a solution of N-tert-butoxycarboxyamino acetic acid (8.76 g) in 3.5 mL of acetonitrile at room temperature is added 8.42 g of 4-nitrobenzylalcohol. To the clear solution is added 0.18 g of N,N-dimethylaminopyridine and a solution of 11.86 g of dicyclohexylcarbodiimide in 15 mL of acetonitrile within 15 minutes maintaining the temperature at 20° C. The resulting suspension is stirred for 2 hours at room temperature and cooled to 0° C. and filtered. The solid is washed with 40 mL of acetonitrile in 4 portions. To the filtrate is added 38.5 mL of a 3.9M solution of hydrochloric acid in ethyl acetate within 20 minutes maintaining the temperature at room temperature. The resulting suspension is stirred for 1 hour at room temperature and the solid collected by filtration. The solid is washed with 80 mL of acetonitrile and dried in vacuum to give 11.9 g of the title compound. $^1$H-NMR, δ d$^6$-DMSO: 8.70-8.50 (3H, Brs, NH$_3$), 8.25 (2H, m, Ph), 7.70 (2H, m, Ph), 5.40 (2H, s, CH$_2$), 3.93 (2H, s, CH$_2$).

In a similar fashion the following gylcine esters can be prepared

Amino acetic acid {1(R)-hydroxy-phenylacetic acid methyl ester}ester hydrochloride. $^1$H-NMR, δ d$^6$-DMSO: 8.75-8.60 (3H, Brs, NH$_3$), 7.50-7.25 (5H, m, Ph), 6.10 (1H, s, CH), 4.25-4.00 (2H, m, CH$_2$N), 3.63 (3H, s, CH$_3$O)

Amino acetic acid {1(S)-hydroxy-phenylacetic acid methyl ester}ester hydrochloride. $^1$H-NMR, δ d$^6$-DMSO: 8.75-8.60 (3H, Brs, NH$_3$), 7.50-7.25 (5H, m, Ph), 6.10 (1H, s, CH), 4.25-4.00 (2H, m, CH$_2$N), 3.63 (3H, s, CH$_3$O).

Amino acetic acid benzhydryl ester hydrochloride. $^1$H-NMR, δ d$^6$-DMSO: 8.50-8.30 (3H, Brs, NH$_3$), 7.50-7.30 (10H, m, 2×Ph), 6.95 (1H, s, CH), 3.70-3.50 (2H, Brs, CH$_2$).

Amino acetic acid adamantan-1-ylmethyl ester hydrochloride. $^1$H-NMR, δ CDCl$_3$: 8.60-8.30 (3H, Brs, NH$_3$), 3.83 (2H, s, CH$_2$O), 3.78 (2H, Brs, CH$_2$), 2.00-1.50 (15H, m).

Amino acetic acid {2(S)-hydroxyphenyethyl}ester hydrochloride. $^1$H-NMR, δ d$^6$-DMSO: 8.55-8.35 (3H, Brs, NH$_3$), 7.45-7.25 (5H, m, Ph), 5.95 (1H, q, CH), 3.90-3.75 (2H, m, CH$_2$N), 1.50 (3H, d, CH$_3$).

Amino acetic acid {2(R)-hydroxyphenyethyl}ester hydrochloride. $^1$H-NMR, δ d$^6$-DMSO: 8.55-8.35 (3H, Brs, NH$_3$), 7.45-7.25 (5H, m, Ph), 5.95 (1H, q, CH), 3.90-3.75 (2H, m, CH$_2$N), 1.50 (3H, d, CH$_3$).

Amino acetic acid (1R,2S,5R)-2-isopropyl-5-methyl-cyclohexyl ester hydrochloride. $^1$H-NMR, δ d$^6$-DMSO: 4.63 (1H, td, CHO), 3.55 (2H, s, NCH$_2$), 1.85 (2H, m, CH$_2$), 1.65 (2H, m, CH$_2$), 1.55-1.25 (2H, m, CH$_2$), 1.15 (2H, m, 2×CH), 0.85 (3H, d, Me), 0.46 (6H, d, Me$_2$).

Amino acetic acid (1S,2R,5S)-5-methyl-2-(1-methyl-1-phenyl-ethyl)-cyclohexyl ester hydrochloride. $^1$H-NMR, δ d$^6$-DMSO: 8.60-8.30 (3H, m, NH$_3$), 7.30 (3H, m, Ph), 7.10 (2H, m, Ph), 4.80 (1H, m, CHO), 3.33 (2H, m, CH$_2$N), 2.62 (1H, d, CH), 2.05 (1H, m, CH), 1.70-0.80 (15H, m).

Amino acetic acid (S)-1,7,7-trimethyl-bicyclo[2.2.1]hept-2-yl ester hydrochloride. $^1$H-NMR, δ d$^6$-DMSO: 8.40-8.20 (3H, Brs, NH$_3$), 4.69 (1H, m, CHO), 3.38 (2H, s, CH$_2$N), 3.30 (4H, s, 2×CH$_2$), 1.80-0.80 (12H, m).

Amino acetic acid isopropyl ester hydrochloride. $^1$H-NMR, δ d$^6$-DMSO: 8.60-8.40 (3H, Brs, NH$_3$), 5.00 (1H, m, CHO), 4.37 (2H, s, CH$_2$N), 3.75 (2H, Brs, CH$_2$) 3.37 (3H, s, MeO), 2.15 (2H, m, CH$_2$), 1.34 (6H, d, 2×Me).

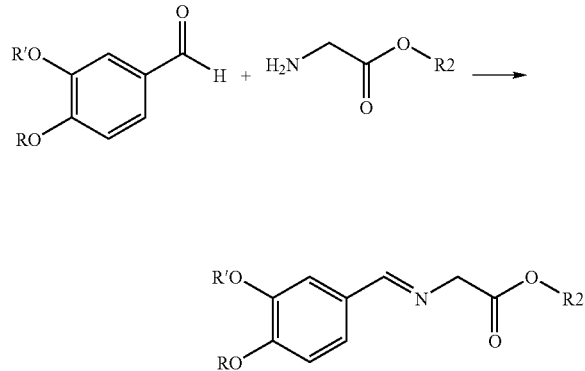

{[1-[4-Methoxy-3-(3-methoxy-propoxy)-phenyl]-meth-(E)-ylidene]-amino}-acetic acid ethyl ester, IIIa R2=Et Glycine ethyl ester hydrochloride salt (6.98 g, 0.05 mol) is suspended in 100 mL of methylene chloride. To the suspension is added a solution of 11.2 g (0.05 mol) of 4-methoxy-3-(3-methoxy-propoxy)-benzaldehyde in 10 mL of methylene chloride followed by 0.5 mol of anhydrous magnesium sulphate. Triethylamine (5.31 g, 0.052 mol) is added within 15 minutes. The suspension is stirred for 24 hours at room temperature and filtered. The solvent is removed in vacuum at room temperature and the residue suspended in tert-butylmethyl ether and stirred for 2 hours and filtered. The solvent is removed in vacuum at room temperature to yield the imine IIIa as a pale yellow oil. $^1$H-NMR, δ CDCl$_3$: 8.10 (1H, s), 7.40 (1H, m), 7.15 (1H, m), 6.78 (1H, m), 4.28 (2H, s), 4.18 (2H, q), 4.10 (2H, t), 3.82 (3H, s), 3.50 (2H, t), 3.25 (3H, s), 2.05 (2H, m), 1.10 (3H, t).

{[1-[4-Methoxy-3-(3-methoxy-propoxy)-phenyl]-meth-(E)-ylidene]-amino}-acetic acid tert-butyl ester, IIIa: prepared as above. $^1$H-NMR, δ CDCl$_3$: 8.18 (1H, s), 7.50 (1H, m), 7.22 (1H, m), 6.90 (1H, m), 4.30 (2H, s), 4.20 (2H, t), 3.92 (3H, s), 3.59 (2H, t), 3.37 (3H, s), 2.14 (2H, m), 1.52 (9H, s).

{[1-[4-Methoxy-3-(3-methoxy-propoxy)-phenyl]-meth-(E)-ylidene]-amino}-acetic acid (1R,2S,5R)-2-isopropyl-5-methyl-cyclohexyl ester IIIa: prepared as above. $^1$H-NMR, δ CDCl$_3$: 8.50 (1H, s), 7.39 (1H, m), 7.25 (1H, m), 7.00 (1H, m), 4.65 (1H, td), 4.34 (2H, ABq), 4.09 (2H, t), 3.82 (3H, s), 3.47 (2H, t), 3.35 (3H, s), 2.05-1.80 (4H, m), 1.63 (2H, m), 1.55-1.35 (4H, m), 1.10-0.95 (5H, m), 0.85 (6H, d), 0.62 (3H, d).

{[1-[4-Methoxy-3-(3-methoxy-propoxy)-phenyl]-meth-(E)-ylidene]-amino}-acetic acid benzyl ester IIIa: prepared as above. $^1$H-NMR, δ CDCl$_3$: 8.20 (1H, s, CH=N), 7.52 (1H, m, Ph), 7.45-7.30 (4H, m, Ph), 7.20 (1H, m, Ph), 6.90 (2H, m, Ph), 5.25 (2H, s, CH$_2$Ph), 4.45 (2H, s, CH$_2$N), 4.20 (2H, t, CH$_2$O), 3.93 (3H, s, MeO), 3.60 (2H, t, CH$_2$O), 3.36 (3H, s, MeO), 2.15 (2H, m, CH$_2$).

{[1-[4-Methoxy-3-(3-methoxy-propoxy)-phenyl]-meth-(E)-ylidene]-amino}-acetic acid isopropyl ester IIIa: prepared as above. $^1$H-NMR, δ CDCl$_3$: 8.20 (1H, s, CHN), 7.51 (1H, m, Ph), 7.21 (1H, m, Ph), 6.90 (1H, s, Ph), 5.12 (1H, m, CHO), 4.37 (2H, s, CH$_2$N), 4.18 (2H, t, CH$_2$O), 3.93 (3H, s, MeO), 3.58 (2H, t, CH$_2$O) 3.37 (3H, s, MeO), 2.15 (2H, m, CH$_2$), 1.28 (6H, d, 2×Me).

{[1-[4-Methoxy-3-(3-methoxy-propoxy)-phenyl]-meth-(E)-ylidene]-amino}-acetic acid (1S,2R,5S)-5-methyl-2-(1-methyl-1-phenyl-ethyl)-cyclohexyl ester IIIa: prepared as above. $^1$H-NMR, δ CDCl$_3$: 8.00 (1H, s, CH=), 7.45 (2H, m, Ph), 7.35-7.25 (5H, m, Ph), 7.18 (2H, m, Ph), 7.00 (1H, m, Ph), 6.88 (2H, m, Ph), 4.40 (1H, m, CHO), 4.20 (4H, m, 2×CH$_2$O), 3.900 (3H, m, MeO), 3.55 (5H, m, CH$_2$O+MeO), 3.35 (3H, d, Me), 3.10 (3H, q, CH$_3$), 2.20-1.40 (8H, m), 1.35 (6H, s, 2×Me), 0.90 (3H, d, CH$_3$).

{[1-[4-Methoxy-3-(3-methoxy-propoxy)-phenyl]-meth-(E)-ylidene]-amino}-acetic acid (R)-bicyclo[2.2.1]hept-2-yl ester IIIa: prepared as above. $^1$H-NMR, δ CDCl$_3$: 8.18 (1H, s, CH=N), 7.50 (1H, m, Ph), 7.18 (1H, m, Ph), 6.39 (1H, m, Ph), 4.77 (1H, dd, CHO), 4.37 (2H, s, CH$_2$), 4.19 (2H, t, CH$_2$O), 3.93 (3H, s, MeO), 3.60 (2H, t, CH$_2$O), 3.38 (3H, s, MeO), 3.10 (1H, q, CH), 2.14 (2H, m, CH$_2$), 1.9-1.65 (4H, m, 2×CH$_2$), 1.58 (1H, m, CH), 1.42 (2H, m, CH$_2$), 1.31-1.5 (2H, m, CH$_2$), 1.00 (3H, s), 0.85 (6H, m, 2×Me).

{[1-[4-Methoxy-3-(3-methoxy-propoxy)-phenyl]-meth-(E)-ylidene]-amino}-acetic acid (S)-1-phenyl-ethyl ester IIIa: prepared as above. $^1$H-NMR, δ CDCl$_3$: 8.18 (1H, s, CH=N), 7.49 (1H, m, Ph), 7.90-7.25 (4H, m, Ph), 7.19 (1H, m, Ph), 6.90 (1H, m, Ph), 6.00 (1H, q, CHO), 4.40 (2H, ABq, CH$_2$N), 4.19 (2H, t, CH$_2$O), 3.93 (3H, s, MeO), 3.60 (2H, t, CH$_2$O), 3.39 (3H, s, MeO); 3.10 (1H, q, CHO), 2.15 (2H, m, CH$_2$O), 1.60 (3H, d, CH$_3$).

{[1-[4-Methoxy-3-(3-methoxy-propoxy)-phenyl]-meth-(E)-ylidene]-amino}-acetic acid (S)-1-phenyl-ethyl ester IIIa: prepared as above. $^1$H-NMR, δ CDCl$_3$: 8.18 (1H, s, CH=N), 7.49 (1H, m, Ph), 7.90-7.25 (4H, m, Ph), 7.19 (1H, m, Ph), 6.90 (1H, m, Ph), 6.00 (1H, q, CHO), 4.40 (2H, ABq, CH$_2$N), 4.19 (2H, t, CH$_2$O), 3.93 (3H, s, MeO), 3.60 (2H, t, CH$_2$O), 3.39 (3H, s, MeO); 3.10 (1H, q, CHO), 2.15 (2H, m, CH$_2$O), 1.60 (3H, d, CH$_3$).

{[1-[4-Methoxy-3-(3-methoxy-propoxy)-phenyl]-meth-(E)-ylidene]-amino}-acetic acid {(S)-mandelic acid methylester}ester IIIa: prepared as above. $^1$H-NMR, δ CDCl$_3$: 8.22 (1H, s, CHN), 7.55-7.31 (5H, m, Ph), 7.20 (1H, m, Ph), 6.85 (2H, m, Ph), 6.05 (1H, s, CHO), 4.55 (2H, s, CH$_2$N), 4.15 (2H, t, CH$_2$O), 3.90 (3H, s, MeO), 3.74 (3H, s, MeO), 3.56 (2H, t, CH$_2$O), 3.35 (3H, s, MeO), 2.15 (2H, m, CH$_2$), {[1-[4-Methoxy-3-(3-methoxy-propoxy)-phenyl]-meth-(E)-ylidene]-amino}-acetic acid 4-nitrobenzyl ester IIIa: prepared as above. $^1$H-NMR, δ CDCl$_3$: 8.31 (1H, s, CHN), 8.23 (2H, m, Ph), 7.40 (2H, m, Ph), 7.40 (1H, m, Ph), 7.28 (1H, m, Ph), 7.03 (1H, m, Ph), 5.32 (2H, s, PhCH), 4.50 (2H, s, CH$_2$N), 4.05 (2H, t, CH$_2$O), 3.82 (3H, s, MeO), 3.48 (2H, t, CH$_2$O) 3.21 (3H, s, MeO), 1.95 (2H, m, CH$_2$), {[1-[4-Methoxy-3-(3-methoxy-propoxy)-phenyl]-meth-(E)-ylidene]-amino}-acetic acid 4-nitrobenzyl ester IIIa: prepared as above. $^1$H-NMR, δ CDCl$_3$: 8.20 (1H, s, CHN), 7.51-7.20, 11H, 2×Ph), 7.00 (1H, s, CH), 6.90 (2H, m, Ph), 4.51 (2H, s, CH$_2$N), 4.19 (2H, t, CH$_2$O), 3.93 (3H, s, MeO), 3.58 (2H, t, CH$_2$O) 3.35 (3H, s, MeO), 2.14 (2H, m, CH$_2$), {[1-[4-Methoxy-3-(3-methoxy-propoxy)-phenyl]-meth-(E)-ylidene]-amino}-acetic acid 1-adamantylmethyl ester IIIa: prepared as above. $^1$H-NMR, δ CDCl$_3$: 8.20 (1H, s, CHN), 7.51 (1H, m, Ph), 7.21 (1H, m, Ph), 6.90 (2H, m, Ph), 4.41 (2H, s, CH$_2$N), 4.19 (2H, t, CH$_2$O), 3.91 (3H, s, MeO), 3.80 (2H, s. CH$_2$O), 3.58 (2H, t, CH$_2$O) 3.38 (3H, s, MeO), 2.14 (2H, m, CH$_2$), 2.00 (3H, Brs, 3×CH), 1.75-1.55 (10H, m, 5×CH$_2$).

4-Acetyl-5-[4-methoxy-3-(3-methoxy-propoxy)-phenyl]-pyrrolidine-2-carboxylic acid ethyl ester, IVa

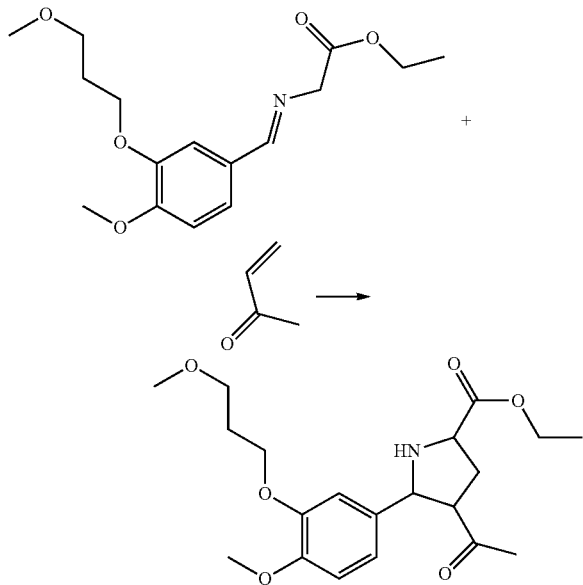

A solution of {[1-[4-Methoxy-3-(3-methoxy-propoxy)-phenyl]-meth-(E)-ylidene]-amino}-acetic acid ethyl ester, IIIa (14.9 g, 0.0482 mol) in 100 mL of toluene is treated with 3.04 g (0.0434 mol) of methyl vinyl ketone. The mixture is cooled to 0° C. and silver acetate (12.1 g) is added. A solution of triethylamine (5.4 g, 0.053 mol) in 10 mL of toluene is added and the mixture warmed to room temperature. The reaction is stirred for 3.5 hours and filtered. The solvent is removed in vacuum to give an oil. This oil can be purified on silica-gel eluting with heptane/ethyl acetate mixtures to give the free pyrrolidine IVa. $^1$H-NMR, CDCl$_3$: 6.80-6.70 (3H, m), 4.21 (1H, d), 4.10 (2H, t), 4.05 (2H, t), 3.85 (1H, t), 3.78 (3H, s), 3.48 (2H, t), 3.35 (1H, m), 3.30 (3H, s), 2.50-2.30 (2H, m, becomes 1H on D$_2$O exchange), 2.21 (1H, m), 2.05 (2H, m), 1.50 (3H, s), 1.10 (3H, t).

4-Acetyl-5-[4-methoxy-3-(3-methoxy-propoxy)-phenyl]-pyrrolidine-2-carboxylic acid ethyl ester hydrochloride salt, IVa(HCl)

The oil from above is re-dissolved in 200 mL of toluene cooled to 0° C. and a solution of HCl gas in ethyl acetate (25.3 mL of a 4.0M solution) is added drop wise. A thick white suspension is formed which is stirred for 30 minutes at room temperature. The suspension is filtered and the solid washed with 300 mL of ethyl acetate in three portions. The solid is dried in vacuum at 30° C. for 24 hours to give the hydrochloride salt containing triethylamine hydrochloride. $^1$H-NMR (of 4.HCl salt), CDCl$_3$: 6.85-6.75 (3H, m), 5.35 (1H, d), 4.70 (1H, dd), 4.39 (2H, m), 4.10 (2H, t), 3.85 (3H, s), 3.78 (1H, m), 3.55 (2H, t), 3.35 (3H, s), 2.80-2.65 (2H, m), 2.10 (2H, m), 1.85 (3H, s), 1.39 (3H, t). can be prepared.

In a similar fashion 4-(S)-Acetyl-5-[4-methoxy-3-(3-methoxy-propoxy)-phenyl]-pyrrolidine-2-carboxylic acid t-butyl ester, IVa is prepared as a racemate from {[1-[4-Methoxy-3-(3-methoxy-propoxy)-phenyl]-meth-(E)-ylidene]-amino}-acetic acid tert-butyl ester. $^1$H-NMR, δ CDCl$_3$: 6.85-6.80 (3H, m, Ph), 4.53 (1H, d, PhCHN), 4.10 (2H, m, CH$_2$O), 3.85-3.80 (4H, m, MeO+NCH), 3.58 (2H, t, CH$_2$O), 3.41 (1H, m, CHCO), 3.35 (3H, s, MeO), 2.30 (2H, m, CH$_2$), 2.10 (2H, m, CH$_2$), 1.65 (3H, s, Me), 1.54 (9H, s, tBu) can be prepared. The 4-acetyl epimer can also be isolated from this reaction: 4-(R)-Acetyl-5-[4-methoxy-3-(3-methoxy-propoxy)-phenyl]-pyrrolidine-2-carboxylic acid t-butyl ester, $^1$H-NMR, δ CDCl$_3$: 6.85 (3H, m, Ph), 4.70 (1H, d, PhCHN), 4.10 (3H, m, CH$_2$O+PhCHN), 3.85 (3H, s, MeO), 3.58 (2H, t, CH$_2$O), 3.36 (4H, s, MeO+CH), 2.26 (1H, m, CH), 2.15-2.00 (3H, m, CH$_2$+CH), 1.63 (3H, s, Me), 1.50 (9H, s, tBu).

(2S,4S,5R)-4-Acetyl-5-[4-methoxy-3-(3-methoxy-propoxy)-phenyl]-pyrrolidine-2-carboxylic acid t-butyl ester Silver acetate (0.085 g, 0.51 mmol) and 267.2 mg of (R)-QUINAP are suspended in 30 mL of dry tetrahydrofuran at room temperature. The mixture is stirred for two hours in the dark after which time a clear solution forms. This catalyst solution is then added to a solution of 6.41 g of {[1-[4-Methoxy-3-(3-methoxy-propoxy)-phenyl]-meth-(E)-ylidene]-amino}-acetic acid tert-butyl ester in 55 mL of tetrahydrofuran at −30° C. within 5 to 10 minutes. Methylvinyl ketone (1.33 g) and Hünig's base (0.246 g) are added and the reaction stirred in the absence of light for 5 days at −30° C.

A solution of ammonium chloride (20 mL, 27% ig) is added and the mixture warmed to room temperature. Ethyl acetate (100 mL) and water (10 mL) are added and the mixture stirred for 15 minutes at room temperature. The organic phase is separated and washed with brine and dried over anhydrous sodium sulphate and the solvent removed under reduced pressure to give an oil.

The oil is dissolved in a 1:1 mixture of tert-butylmethyl ether and ethyl acetate and stirred at room temperature for 24 hours, filtered and the solvent removed in vacuum. The residue (7.56 g) is then taken up in 30 mL of di-isopropylether and the suspension stirred for 2 hours at room temperature. The solid is collected by filtration and washed with 2×9 mL of diisopropylether and dried at 30° C. in vacuum overnight to give 4 g of the desired compound with an % ee of 79%. A second re-crystallisation from di-isopropylether raises the % ee to >97%. [α]d=+47.1° (1% CHCl$_3$).

Replacement of (R)-QUINAP with (S)-QUINAP produces the other enantiomer, (2R,4R,5S)-4-Acetyl-5-[4-methoxy-3-(3-methoxy-propoxy)-phenyl]-pyrrolidine-2-carboxylic acid t-butyl ester, [α]d=−47.1° (1% CHCl$_3$).

(2S,4S,5R)-4-Acetyl-5-[4-methoxy-3-(3-methoxy-propoxy)-phenyl]-pyrrolidine-2-carboxylic acid (1R,2S,5R)-2-isopropyl-5-methyl-cyclohexyl ester and (2R,4R,5S)-4-Acetyl-5-[4-methoxy-3-(3-methoxy-propoxy)-phenyl]-pyrrolidine-2-carboxylic acid (1R,2S,5R)-2-isopropyl-5-methyl-cyclohexyl ester. A solution of 13.7 g of {[1-[4-Methoxy-3-(3-methoxy-propoxy)-phenyl]-meth-(E)-ylidene]-amino}-acetic acid (1R,2S,5R)-2-isopropyl-5-methyl-cyclohexyl ester in 50 mL of toluene is treated with 2.10 g of Methylvinyl ketone at room temperature. Silver acetate (0.15 g), triphenylphosphine (0.24 g) and quinine (0.29 g) are added sequentially and the mixture stirred in the absence of light for 24 hours at room temperature. A solution of ammonium chloride (25 mL, 27%) and 10 mL of water is added and the mixture extracted. The organic phase is separated and the solvent removed in vacuum to give a semi-solid. This is stirred in 150 mL of tert-butylmethyl ether at room temperature, filtered and the solid washed with 2×20 mL of tert-butylmethyl ether and dried in vacuum to give 4.69 g of the desired compounds as a mixture of diastereoisomers, around 78% ee of the desired (2S,4S,5R)-4-Acetyl-5-[4- methoxy-3-(3-methoxy-propoxy)phenyl]-pyrrolidine-2-carboxylic acid (1R,2S,5R)-2-isopropyl-5-methyl-cyclohexyl ester being present. The mother liquor was evaporated to give a semi solid, which is stirred for 2 hours at room temperature in 50 mL of di-isopropylether. Filtration and drying produced 2.92 g of a solid containing around 65% ee of the other diastereoisomer.

The solid containing 78% ee of (2S,4S,5R)-4-Acetyl-5-[4-methoxy-3-(3-methoxypropoxy)-phenyl]-pyrrolidine-2-carboxylic acid (1R,2S,5R)-2-isopropyl-5-methyl-cyclohexyl ester, (4.10 g) is dissolved in 120 mL of isopropanol at 70° C. and filtered. The solid is washed with 2×20 mL of hot isopropanol and the filtrate cooled to room temperature within 4 hours and stirred for a further 4 hours. The solid is collected by filtration and washed twice with 20 mL of isopropanol. After drying for 24 hours at 35° C. in vacuum 2.19 g of (2S,4S,5R)-4-Acetyl-5-[4-methoxy-3-(3-methoxy-propoxy)-phenyl]-pyrrolidine-2-carboxylic acid (1R,2S,5R)-2-isopropyl-5-methyl-cyclohexyl ester is obtained with a specific rotation of −66° (1% in chloroform) and a M.Pt. of 136.4° C. corresponding to an ee of 99%. $^1$H-NMR, δ CDCl$_3$ 6.90-6.80 (3H, m, Ph), 4.90-4.79 (1H, td, CHO), 4.53 (1H, d, PhCHN), 4.12 (2H, t, CH2O), 3.95-3.86 (1H, m, NCHCO), 3.86 (3H, s, MeO), 3.59 (2H, t, CH$_2$O), 3.44 (1H, m, CHCO), 3.38 (3H, s, MeO), 2.43-2.25 (2H, m, CH$_2$), 2.11 (3H, m, CH$_2$+CH), 1.95 (1H, m, CH), 1.72 (2H, m, CH$_2$), 1.66 (3H, s, COCH$_3$), 1.61-1.40 (2H, m), 1.17-0.99 (2H, m), 0.97-0.88 (7H, m, $^i$Pr+CH), 0.82 (3H, d, Me)

The other isomer may be obtained by re-crystallisation of 65% ee material from 100 mL of hot di-isopropylether. (2R,4R,5S)-4-Acetyl-5-[4-methoxy-3-(3-methoxy-propoxy)phenyl]-pyrrolidine-2-carboxylic acid (1R,2S,5R)-2-isopropyl-5-methyl-cyclohexyl ester, 1.53 g with a specific rotation of −13.4° (1% in chloroform), corresponding to an % ee of 87%. $^1$H-NMR, δ CDCl$_3$ 6.85 (3H, m, Ph), 4.83 (1H, td, J=11 & 4 Hz, CHO), 4.53 (1H, d, J=8.1 Hz, PhCHN), 4.11 (1H, td, J=6.58 & 2.5 Hz, CHO), 3.91 (2H, t, CH$_2$O), 3.86 (3H, s, MeO), 3.59 (2H, t, CH$_2$O), 3.44 (1H, m, CHCO), 3.38 (3H, s, MeO), 2.95-2.50 (1H, Brs, NH), 2.36 (2H, ABq, CH$_2$), 2.11 (3H, m, CH$_2$+CH), 1.96 (1H, m, CH), 1.72 (2H, m, CH$_2$), 1.67 (3H, s, COCH$_3$), 1.60-1.42 (2H, m), 0.93 (6H, m, $^i$Pr), 0.83 (3H, d, Me)

In a similar fashion 4(R)-Acetyl-5-[4-methoxy-3-(3-methoxy-propoxy)-phenyl]-pyrrolidine-2-carboxylic acid benzhydryl ester, IVa is prepared as a racemate from {[1-[4-Methoxy-3-(3-methoxy-propoxy)-phenyl]-meth-(E)-ylidene]-amino}-acetic acid benzhydryl ester. $^1$H-NMR, δ CDCl$_3$: 7.45-7.25 (10H, m, Ph), 7.01 (1H, Brs, NH), 6.80 (3H, m, Ph), 4.55 (1H, d, NCHCO), 4.10-4.03 (3H, m, CH$_2$O), 3.45 (1H, q, CHCO), 3.35 (3H, s, MeO), 2.45 (1H, dd, CH), 2.35 (1H, dd, CH), 2.10-2.05 (5H, m, CH$_2$+CH$_3$), 1.65 (3H, s, CH$_3$). The epimer at the 4 position, 4(S)-Acetyl-5-[4-methoxy-3-(3-methoxy-propoxy)-phenyl]-pyrrolidine-2-carboxylic acid benzhydryl ester $^1$H-NMR, δ CDCl$_3$: 7.40-7.25 (10H, m, Ph), 6.941 (1H, Brs, NH), 6.80 (3H, m, Ph), 4.68 (1H, d, NCHCO), 4.35 (1H, dd, PhCHN), 4.10-4.03 (3H, m, CH$_2$O+CH), 3.85 (3H, s, MeO), 3.8 (2H, t, CH$_2$C), 3.38-3.30 (4H, m, MeO+CHCO), 2.75 (2H, m, CH$_2$), 2.08 (5H, m, CH$_2$+CH$_3$), 1.58 (3H, s, CH$_3$), can also be isolated from this reaction.

In a similar fashion, 4-Acetyl-5-[4-methoxy-3-(3-methoxy-propoxy)-phenyl]-pyrrolidine-2-carboxylic acid 4-nitrobenzyl ester $^1$H-NMR, δ CDCl$_3$: 7.40 (5H, m, Ph), 7.05 (1H, m, Ph), 6.95 (1H, m, Ph), 6.82 (1H, m, Ph), 5.22 (2H, m, PhCH$_2$), 4.21 (1H, d, PhCHN), 4.15-4.00 (3H, m, CH$_2$O+CHN), 3.86 (3H, s, MeO), 3.57 (2H, t, CH$_2$O), 3.35 (3H, s, MeO), 3.10 (1H, m, CHCO), 2.75-2.25 (3H, m, CH$_2$+NH), 2.12 (2H, m, CH$_2$), 2.00 (3H, s, CH$_3$), can be prepared.

In a similar fashion, 4-Acetyl-5-[4-methoxy-3-(3-methoxy-propoxy)-phenyl]-pyrrolidine-2-carboxylic acid adamantan-1-ylmethyl ester $^1$H-NMR, δ CDCl$_3$: was not formed.

In a similar fashion, 4-Acetyl-5-[4-methoxy-3-(3-methoxy-propoxy)-phenyl]-pyrrolidine-2-carboxylic acid (S)-1,7,7-trimethyl-bicyclo[2.2.1]hept-2-yl ester hydrochloride $^1$H-NMR, δ d$^6$DMSO: 9.50-9.20 (2H, Brs NH$^+_2$), 7.45 (1H, m, Ph), 7.25-7.10 (2H, m, Ph), 4.95-4.70 (3H, m, CHO+PhCHN+NCHCO), 4.20 (2H, t, CH$_2$O), 3.95 (3H, s, MeO), 3.65 (2H, t, CH$_2$O), 3.51 (3H, s, MeO), 3.25 (2H, m, CH$_2$), 3.09 (2H, m, CH$_2$), 2.30 (3H, s, Me), 2.2 (2H, m, CH$_2$), 2.15 (2H, m, CH$_2$), 2.05-1.65 (3H, m), 1.10 (3H, s, Me), 0.95 (3H, s, Me), can be prepared.

In a similar fashion, 4-Acetyl-5-[4-methoxy-3-(3-methoxy-propoxy)-phenyl]-pyrrolidine-2-carboxylic acid (R)-methoxycarbonyl-phenyl-methyl ester $^1$H-NMR, δ d$^6$DMSO: 7.80-7.35 (6H, m, NH$^+_2$+Ph), 7.30-7.15 (3H, m, Ph), 6.85 (1H, m, Ph), 6.12 (1H, s, CHO), 4.30-4.10 (3H, m, CH$_2$O+PhCH), 3.90 (3H, s, MeO), 3.81 (3H, m, MeO), 3.60 (2H, t, CH$_2$O), 3.40 (3H, s, MeO), 3.20 (1H, m, CHCO), 2.20 (2H, m, CH$_2$), can be prepared.

In a similar fashion, 4-Acetyl-5-[4-methoxy-3-(3-methoxy-propoxy)-phenyl]-pyrrolidine-2-carboxylic acid benzyl ester, IVa is prepared as a racemate from {[1-[4-Methoxy-3-(3-methoxy-propoxy)-phenyl]-meth-(E)-ylidene]-amino}-acetic acid benzyl ester. $^1$H-NMR, δ CDCl$_3$: 7.40 (5H, m, Ph), 7.05 (1H, m, Ph), 6.95 (1H, m, Ph), 6.82 (1H, m, Ph), 5.22 (2H, m, PhCH$_2$), 4.21 (1H, d, PhCHN), 4.15-4.00 (3H, m, CH$_2$O+CHN), 3.86 (3H, s, MeO), 3.57 (2H, t, CH$_2$O), 3.35 (3H, s, MeO), 3.10 (1H, m, CHCO), 2.75-2.25 (3H, m, CH$_2$+NH), 2.12 (2H, m, CH$_2$), 2.00 (3H, s, CH$_3$), can be prepared.

In a similar fashion using (R)-QUINAP, (2S,4S,5R)-4-Acetyl-5-[4-methoxy-3-(3-methoxypropoxy)-phenyl]-pyrrolidine-2-carboxylic acid isopropyl ester, $^1$H-NMR, δ CDCl$_3$: 6.89-6.79 (3H, m, Ph), 5.15 (1H, m, CHO), 4.52 (1H, d, PHCHN), 4.11 (2H, t, CH$_2$O), 3.85 (3H, s, MeO), 3.60 (2H, t, CH$_2$O), 3.41 (1H, m, CHCO), 3.48 (3H, s, MeO), 2.39 (1H, ddd, CH), 2.29 (1H, ddd, CH), 2.12 (2H, m, CH$_2$), 1.30 (6H, 2 overlapping d, 2×Me), can be prepared. The epimer (2R,4R,5S)-4-Acetyl-5-[4-methoxy-3-(3-methoxy-propoxy)-phenyl]-pyrrolidine-2-carboxylic acid isopropyl ester, can also be isolated; $^1$H-NMR, δ CDCl$_3$: 6.89-6.79 (3H, m, Ph), 5.15 (1H, m, CHO), 4.52 (1H, d, PHCHN), 4.11 (2H, t, CH$_2$O), 3.85 (3H, s, MeO), 3.60 (2H, t, CH$_2$O), 3.41 (1H, m, CHCO), 3.48 (3H, s, MeO), 2.39 (1H, ddd, CH), 2.29 (1H, ddd, CH), 2.12 (2H, m, CH$_2$), 1.30 (6H, 2 overlapping d, 2×Me).

(2S,4S,5R)-4-Acetyl-5-[4-methoxy-3-(3-methoxy-propoxy)-phenyl]-pyrrolidine-1,2-dicarboxylic acid 1-tert-butyl ester 2-ethyl ester and (2R,4R,5S)-4-Acetyl-5-[4-methoxy-3-(3-methoxy-propoxy)-phenyl]-pyrrolidine-1,2-dicarboxylic acid 1-tert-butyl ester 2-ethyl ester

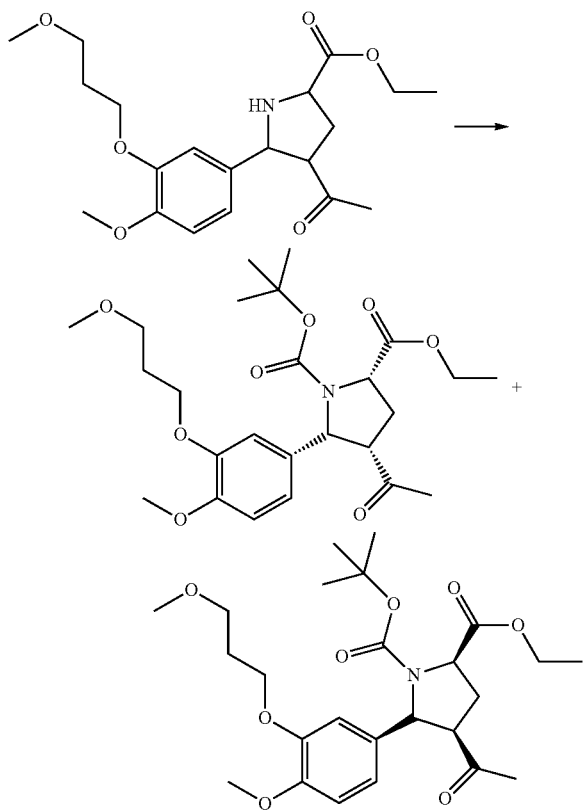

4-Acetyl-5-[4-methoxy-3-(3-methoxy-propoxy)-phenyl]-pyrrolidine-2-carboxylic acid ethyl ester hydrochloride salt, IVa(HCl) (17.7 g, 0.0425 mol) is suspended in 250 mL of ethyl acetate at room temperature. Hünig's base (10.7 g, 0.083 mol) is added dropwise followed by 0.1 g of 4-N,N-dimethylaminopyridine. The mixture is treated with a solution of Boc$_2$O (9.27 g, 0.0425 mol) in 20 mL of ethyl acetate. The reaction mixture is stirred for 1 hour at room temperature and treated with 200 mL of 10% aqueous citric acid. The organic phase is separated and washed twice with 300 mL of water containing 10 mL of saturated aqueous sodium hydrogen carbonate solution followed by a 300 mL water wash. The organic phase is dried over anhydrous sodium sulphate and filtered. The solvent is removed in vacuum at 35° C. to give 16.2 g of an oil. This oil is purified by chromatography on silica-gel eluting with ethyl acetate/heptane mixtures producing the title compound. $^1$H-NMR, CDCl$_3$: 7.15 (1H, m), 6.85 (1H, m), 6.65 (1H, m), 5.11 & 5.05 (1H, d, rotamers), 4.30-4.10 (3H, m), 4.05 (2H, t), 3.75 (3H, s), 3.50 (2H, t), 3.38 (1H, m), 3.25 (3H, s), 2.50 (1H, m), 2.20 (1H, m), 2.05 (2H, m), 1.80 & 1.75 (3H, s rotamers), 1.25 & 1.15 (9H, s, rotamers), 1.25 (3H, t).

A solution of 1 g of this oil is dissolved in 12 mL of a mixture of hexane/ethanol/acetonitrile (7/4/1) and applied to a Chiralpack AD-H 30×250 mm chromatography column and eluted with a mixture of CO2 and hexane/ethanol (8/2). (2R,4R,5S)-4-Acetyl-5-[4-methoxy-3-(3-methoxy-propoxy)-phenyl]-pyrrolidine-1,2-dicarboxylic acid 1-tert-butyl ester 2-ethyl ester is eluted first from the column, retention time, 1.83 minutes, specific rotation=+16.8° (1% in chloroform), followed by (2S,4S,5R)-4-Acetyl-5-[4-methoxy-3-(3-methoxypropoxy)-phenyl]-pyrrolidine-1,2-dicarboxylic acid 1-tert-butyl ester 2-ethyl ester retention time, 2.02 minutes, specific rotation=−17.6° (1% in chloroform).

(2S,4S,5R)-4-Acetyl-5-[4-methoxy-3-(3-methoxy-propoxy)-phenyl]-pyrrolidine-1,2-dicarboxylic acid 1-tert-butyl ester 2 t-butyl ester. (2S,4S,5R)-4-Acetyl-5-[4-methoxy-3-(3-methoxy-propoxy)-phenyl]-pyrrolidine-2-carboxylic acid t-butyl ester (10.0 g, 0.02455 mol) is suspended in 175 mL of ethyl acetate at room temperature followed by 0.1 g of 4-N,N-dimethylaminopyridine. The mixture is treated with a solution of Boc$_2$O (5.36 g, 0.0425 mol) in 20 mL of ethyl acetate. The reaction mixture is stirred for 1 hour at room temperature and treated with 200 mL of 10% aqueous citric acid. The organic phase is separated and washed twice with 300 mL of water containing 10 mL of saturated aqueous sodium hydrogen carbonate solution followed by a 300 mL water wash. The organic phase is dried over anhydrous sodium sulphate and filtered. The solvent is removed in vacuum at 35° C. to give 16.2 g of an oil. This oil is purified by chromatography on silica-gel eluting with ethyl acetate/heptane mixtures producing the title compound. $^1$H-NMR, CDCl$_3$: 7.18 (1H, m, Ph), 7.04 (1H, m, Ph), 6.79 (1H, m, Ph), 5.32 & 5.13 (1H, PhCHN, rotamers), 4.22 (1H, m, NCHCO$_2$), 4.14 (2H, t, CH$_2$O), 3.84 (3H, m, CH$_3$O), 3.58 (2H, t, CH$_2$O), 3.44 (1H, m, CH$_2$O), 3.37 (3H, s, MeO), 2.56 (1H, m, CH), 2.31 (1H, m, CH), 2.10 (2H, m, CH$_2$), 1.90 & 1.84 (3H, s, Me rotamers), 1.55 (9H, s, tBu-ester), 1.43 & 1.25 (9H, s, tBu carbamate rotamers). Specific rotation +13.4° (1% in chloroform)

In a similar fashion (2S,4S,5R)-4-Acetyl-5-[4-methoxy-3-(3-methoxy-propoxy)phenyl]-pyrrolidine-1,2-dicarboxylic acid 1-tert-butyl ester benzyl ester can be prepared from 4-Acetyl-5-[4-methoxy-3-(3-methoxy-propoxy)-phenyl]-pyrrolidine-2-carboxylic acid benzyl ester, $^1$H-NMR, δ CDCl$_3$: 7.40 (5H, m, Ph), 7.19 (1H, m, Ph), 7.00 & 6.95 (1H, m, Ph rotamers), 6.80 (1H, m, Ph), 5.45-5.15 (3H, m, PhCH & PhCH$_2$), 4.45 & 4.35 (1H, m, NCHCO$_2$— rotamers), 4.10 (2H, m, CH$_2$O), 3.84 (3H, s, MeO), 3.58 (2H, t, CH$_2$O), 3.49 (1H, S, CHCO), 3.35 (3H, s, MeO), 2.62 (2H, m, CH$_2$-ring), 2.30 (2H, m, CH$_2$), 2.09 (3H, s, CH$_3$), 1.35-1.20 (9H, m, t-Bu rotamers).

Other N-Boc s in here (2S,4R,5R)-4-Isopropenyl-5-[4-methoxy-3-(3-methoxy-propoxy)-phenyl]-pyrrolidine-1,2-dicarboxylic acid 1-tert-butyl ester 2-ethyl ester VIIa

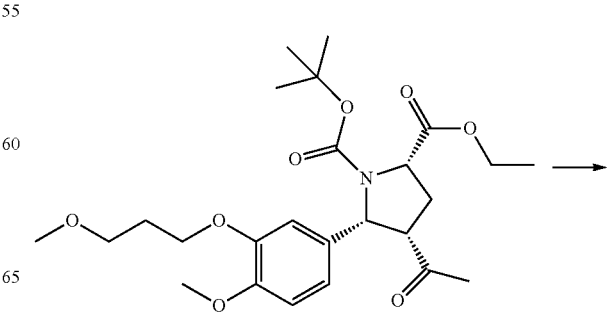

41

-continued

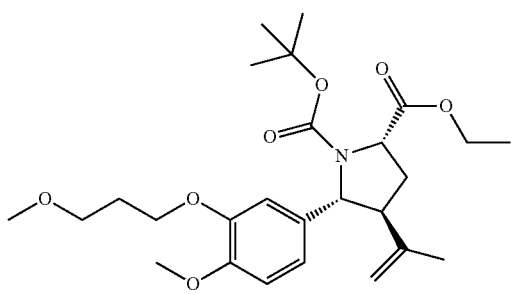

A suspension of 0.104 g (0.0026 mol) of a 60% suspension of sodium hydride in mineral oil in 20 mL of tetrahydrofuran is treated with 0.89 g (0.0025 mol) of methyltriphenylphosphonium bromide. The white suspension is heated to 50° C. and stirred for 7 hours at this temperature. The red suspension is cooled to 0° C. and a solution of (2S,4S,5R)-4-Acetyl-5-[4-methoxy-3-(3-methoxy-propoxy)-phenyl]-pyrrolidine-1,2-dicarboxylic acid 1-tert-butyl ester 2-ethyl ester (0.60 g, 0.00125 mol) dissolved in 5 mL of tetrahydrofuran is added. The mixture is stirred for 1.5 hours at 0° C. and diluted with 20 mL of tert-butylmethyl ether. A 10% aqueous solution of citric acid (25 mL) is added and the mixture extracted. The aqueous phase is re-extracted with a further 20 mL of tert-butyl methyl ether and the organic phases combined. The combined organic phases are washed with 20 mL of water containing 10 mL of saturated aqueous sodium hydrogen carbonate followed by 30 mL of water. The organic phase is dried and the solvent removed in vacuum at 30° C. to give the crude product as an oil. This oil is chromatographed over silica-gel, eluting with heptane/ethyl acetate (4/1) to give the desired product.

$^1$H-NMR, δ CDCl$_3$: 7.30 (1H, m), 6.95 (1H, m), 6.75 (1H, m), 4.80 & 4.65 (2H, olefin rotamers), 4.70 & 4.50 (1H, d, PhCHN rotamers), 4.39 (1H, m, NCHCO$_2$Et), 4.25 (2H, m, ester CH2), 4.15 (2H, m), 3.82 (3H, s), 3.55 (2H, m), 3.30 (3H, s), 2.80 & 2.65 (1H, m, allyl CH rotamers), 2.30-2.05 (4H, m), 1.75 & 1.68/3H, s, acetyl CH$_3$ rotamers), 1.38 & 1.10 (9H, Boc rotamers), 1.25 (3H, t, ester CH$_3$).

In a similar fashion, (2S,4R,5R)-4-Isopropenyl-5-[4-methoxy-3-(3-methoxy-propoxy)phenyl]-pyrrolidine-1,2-dicarboxylic acid 1-tert-butyl ester 2-tert-butyl ester $^1$H-NMR, δ CDCl$_3$: 7.39 & 7.30 (1H, m, Ph rotamers), 7.05 & 7.00 (1H, m, Ph rotamers), 6.80 (1H, Brm, Ph), 4.85 & 4.70 (2H, olefin rotamers), 4.45 & 4.41 (1H, d, PhCHN rotamers), 4.15 (2H, m, NCHCO$_2$Et), 3.85 (3H, s, MeO), 3.58 (2H, m), 3.35 (3H, s, MeO), 2.78 & 2.68 (1H, m, allyl CH rotamers), 2.25-2.05 (4H, m), 1.75 & 1.68 (3H, s, CH$_3$ rotamers), 1.38 & 1.10 (9H, Boc rotamers), can be prepared

42

(2S,4S,5R)-4-Isopropyl-5-[4-methoxy-3-(3-methoxy-propoxy)-phenyl]-pyrrolidine-1,2-dicarboxylic acid 1-tert-butyl ester 2-ethyl ester VIIIa

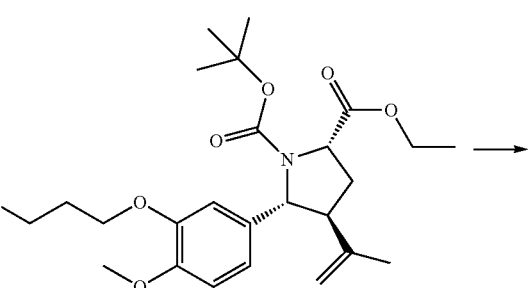

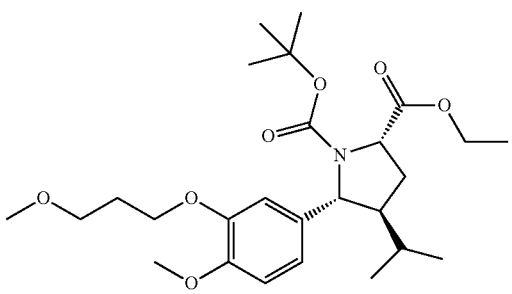

A solution of (2S,4R,5R)-4-Isopropenyl-5-[4-methoxy-3-(3-methoxy-propoxy)-phenyl]-pyrrolidine-1,2-dicarboxylic acid 1-tert-butyl ester 2-ethyl ester VIIa (0.3 g) in 10 mL of toluene is treated with 50 mg of 5% palladium on carbon. The suspension is stirred under an atmosphere of hydrogen for 2 hours at room temperature and filtered. The solvent is removed in vacuum to give the desired compound as an oil.

$^1$H-NMR, δ CDCl$_3$: 7.30 (1H, m), 6.95 (1H, m), 6.75 (1H, m), 4.70 & 4.50 (1H, d, PhCHN rotamers), 4.39 (1H, m, NCHCO$_2$Et), 4.25 (2H, m, ester CH$_2$), 4.15 (2H, m), 3.82 (3H, s), 3.55 (2H, m), 3.30 (3H, s), 2.80 & 2.65 (1H, m, allyl CH rotamers), 2.30-2.05 (5H, m), 1.95 (1H, m), 1.38 & 1.10 (9H, Boc rotamers), 1.25 (3H, t, ester CH$_3$), 0.95 (6H, d isopropyl CH$_3$).

In a similar fashion (2S,4S,5R)-4-Isopropyl-5-[4-methoxy-3-(3-methoxy-propoxy)phenyl]-pyrrolidine-1,2-dicarboxylic acid 1-tert-butyl ester 2-tert-butyl ester $^1$H-NMR, δ CDCl$_3$: 7.41 & 7.35 (1H, m, Ph rotamers), 7.05 (1H, m, Ph), 6.80 (1H, m, Ph), 4.60 & 4.38 (1H, d, PhCHN rotamers), 4.30 (1H, m, NCHCO$_2$Et), 4.18 (2H, t, CH$_2$O), 3.90 & 3.85 (3H, s, MeO rotamers), 3.82 (3H, s), 3.71 (1H, m), 3.58 (2H, t, CH$_2$O), 3.35 (3H, s, MeO), 2.20-1.90 (5H, m), 1.60 (1H, m), 1.50 & 1.40 (9H, Boc rotamers), 1.24 & 1.15 (9H, m, tBu rotamers), 0.95 & 0.88 (6H, d isopropyl CH₃), can be prepared (2R,3S,5S)-5-Hydroxymethyl-3-isopropyl-2-[4-methoxy-3-(3-methoxy-propoxy)-phenyl]-pyrrolidine-1-carboxylic acid tert-butyl ester IXa

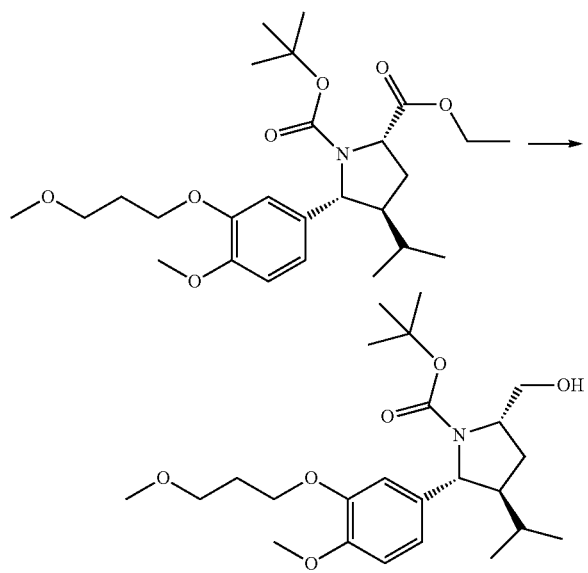

A solution of 0.48 g of (2S,4S,5R)-4-Isopropyl-5-[4-methoxy-3-(3-methoxy-propoxy)-phenyl]-pyrrolidine-1,2-dicarboxylic acid 1-tert-butyl ester 2-ethyl ester VIIIa in 10 mL of tetrahydrofuran is cooled to 0° C. and a tetrahydrofuran solution of lithium borohydride (1.0 mL of a 2.0M solution) is added dropwise within 30 minutes. The mixture is stirred for a further 2 hours at 0° C. and quenched by addition of 0.2 mL of glacial acetic acid in 10 mL of tetrahydrofuran. The mixture is diluted with 20 mL of tert-butyl methyl ether and 20 mL of water and the organic phase separated. The organic phase is dried and the solvent removed to give the desired product as an oil. ¹H-NMR δ (d⁶-DMSO/D₂O, 300K) 6.90-6.80 (3H), 4.03-3.90 (3H), 3.80 (1H), 3.75 (3H), 3.55-3.45 (3H), 3.23 (3H), 3.05 (1H), 2.00-1.80 (3H), 1.65 (1H), 1.40 (9H), 1.20 (1H), 0.74 (6H).

(2S,4R,5R)-4-Acetyl-5-[4-methoxy-3-(3-methoxy-propoxy)-phenyl]-pyrrolidine-1,2-dicarboxylic acid 1-tert-butyl ester XIIa

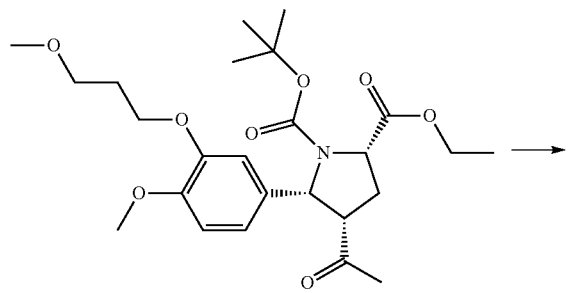

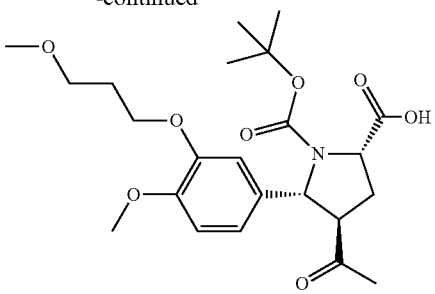

A solution of 0.60 g of (2S,4S,5R)-4-Acetyl-5-[4-methoxy-3-(3-methoxy-propoxy)-phenyl]-pyrrolidine-1,2-dicarboxylic acid 1-tert-butyl ester 2-ethyl ester VIIIa in 10 mL of tetrahydrofuran at room temperature is treated with 2 mL of a 2.0M solution of lithium hydroxide. The solution is stirred for 24 hours at room temperature and diluted with 10 mL of tert-butylmethyl ether and 10 mL of water. The organic layer is removed and the aqueous layer treated with 3 mL of 2.0M hydrochloric acid. The organic phase is separated and washed with 20 mL of water in two portions. The organic layer is dried and the solvent removed in vacuum at 35° C. to give acid XIIa as a white solid. ¹H-NMR δ (d⁶-DMSO): 12.90 (1H, Brs, exch D₂O, CO₂H), 7.45 (1H, m, Ph), 7.05 (1H, m, Ph), 6.90 (1H, m. Ph), 5.05 & 4.80 (1H, d, PhCHN rotamers), 4.30 & 4.15 (1H, m NCHCO₂ rotamers), 4.00 (2H, m, CH₂O), 3.78 (3H, s, CH₃O), 3.50 (2H, s, CH₂O), 3.33 (3H, s, CH₃O), 3.20 (1H, m, CHCO), 2.40 (1H, m, CH), 2.22 & 2.13 (3H, s, Me rotamers), 2.10 (1H, m, CH), 1.95 (2H, m, CH₂), 1.40 & 1.05 (9H, s, tBu rotamers).

The other isomer at position 4 may be prepared as follows: A solution of (2S,4R,5R)-4-Acetyl-5-[4-methoxy-3-(3-methoxy-propoxy)-phenyl]-pyrrolidine-1,2-dicarboxylic acid 1-tert-butyl ester benzyl ester (0.58 g) in 8 mL of methanol is treated with 0.058 g of 10% Pd/C and placed under an atmosphere of hydrogen for 90 minutes at room temperature. The catalyst is removed by filtration and the solvent removed completely to give 0.44 g of the desired compound as a viscous oil. ¹H-NMR δ (d⁶-DMSO): 12.90 (1H, Brs, exch D₂O, CO₂H), 7.40 (1H, m, Ph), 6.95 (1H, m, Ph), 6.80 (1H, m. Ph), 5.17 (1H, d, PhCHN), 4.13 (1H, m NCHCO₂), 4.01 (2H, m, CH₂O), 3.73 (3H, s, CH₃O), 3.55-3.45 (3H, m, CHCO+CH₂O), 3.25 (3H, s, CH₃O), 2.40-2.15 (2H, s, CH₂-ring), 1.93 (2H, m, CH₂), 1.85 (3H, s, Me), 1.28 (9H, s, tBu).

Synthesis of (2R,3S,5S)-5-Formyl-3-isopropyl-2-[4-methoxy-3-(3 methoxy-propoxy)phenyl]pyrrolidine-1-carboxylic acid tert-butyl ester Xa

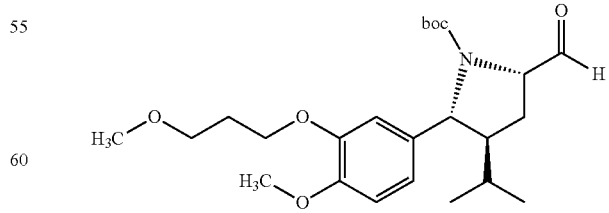

A solution of 4.7 g of alcohol IXa in 58 ml of methylene chloride is treated with 33 mL of dimethylsulphoxide and 5.67 g of triethylamine is added. The mixture is cooled to 0° C. and a solution of 6.84 g of the SO₃/pyridine complex dissolved in 46 mL of dimethyl sulphoxide is added dropwise within 20 minutes. The reaction is stirred at 0° C. for 2 hours and quenched with 105 mL of water and 105 mL of heptane. The organic layer is separated and washed with 25 mL of 10% aqueous sodium hydrogen sulphate solution. The organic phase is then washed with 110 mL of water followed by 25 mL of saturated aqueous sodium hydrogen carbonate solution. Finally the organic phase is washed with water until the pH of the aqueous solution is 7. The solvent is then removed to give the aldehyde Xa as an oil. A negative $[a]_d$ is found at c=1, CHCl$_3$. $^1$H-NMR δ (d$^6$-DMSO, 300K) 9.75 (1H), 6.90-6.80 (3H), 4.63-4.30 (3H), 4.00 (2H), 3.75 (3H), 3.50 (3H), 3.23 (3H), 2.10-1.90 (4H), 1.85 (1H), 1.60 (1H), 1.05 (9H), 0.85 (6H).

Synthesis of (2R,3S,5S)-5-((1S,3S)-3-Benzyloxymethyl-1-hydroxy-4-methyl-pentyl)-3-isopropyl-2-[4-methoxy-3-(3 methoxy-propoxy)-phenyl]pyrrolidine-1-carboxylic acid tert-butyl ester XVa

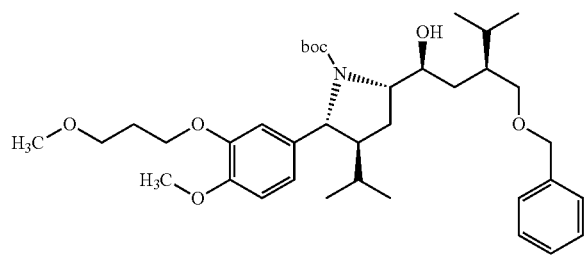

A solution of 1.98 g of aldehyde Xa in 15 mL of tetrahydrofuran is cooled to 10° C. and is treated with the Grignard reagent prepared by treating 1.23 g of ((S)-2-bromomethyl-3-methyl-butoxymethyl)-benzene with 0.12 g of magnesium in diethylether containing 0.043 g of 1,2-dibromoethane at 45° C. The reaction is stirred for 90 minutes at room temperature, then 20 mL of a 25% aqueous solution of ammonium chloride is added, followed by addition of 20 mL of tert-butylmethyl ether. The organic phase is separated and washed twice with 20 mL of water. The organic phase is concentrated in vacuum to give the crude alcohol XVa as an oil. Purification on silica-gel delivers e.g. 0.97 g of pure XVa. A negative $[a]_d$ is found at c=1, CHCl$_3$.
M$^+$+H=628, M$^+$+H+Na=650.

Synthesis of (2R,3S,5S)-5-((1S,3S)-1-Hydroxymethyl-3-hydroxymethyl-4-methylpentyl)-3-isopropyl-2-[4-methoxy-3-(3 methoxy-propoxy)-phenyl]pyrrolidine-1-carboxylic acid tert-butyl ester XVIa

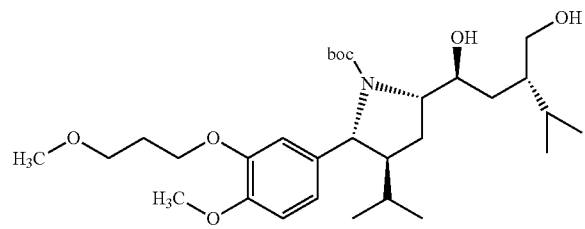

A solution of 0.48 g of XVa in 1.5 mL of methanol is treated with 0.1 g of 10% palladium on charcoal. The suspension is stirred under an atmosphere of hydrogen until the uptake is stable. The suspension is filtered and the solid washed with 5 mL of methanol in two portions. Removal of the solvent in vacuum provides alcohol XVIa as an oil. A negative $[a]_d$ (e.g. −34.1, −34.6) is found at c=1, CHCl$_3$.

Synthesis of (2R,3S,5S)-5-((2S,4S)-5-Hydroxy-4-isopropyl-tetrahydro-furan-2-yl)-3-isopropyl-2-[4-methoxy-3-(3-methoxypropoxy)-phenyl]-pyrrolidine-1-carboxylic acid tert-butyl ester XVIIIa

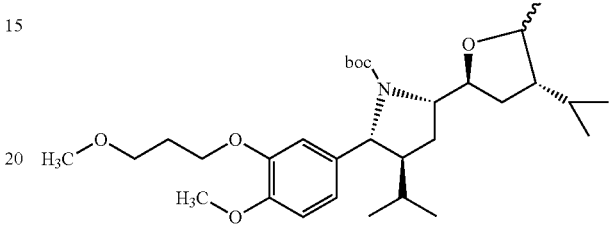

Variant employing SO$_3$/pyridine: A solution of 0.20 g of alcohol XVIa in 5 mL of methylene chloride is treated with 3 mL of dimethyl sulphoxide and 0.2 g of triethylamine at 0° C. A solution of 0.24 g of the SO$_3$/pyridine complex in 4 mL of dimethyl sulphoxide is added dropwise within 15 minutes at 0° C. The reaction is stirred for 40 minutes at 0° C. then warmed to room temperature and stirred for a further 2 hours.

Water (10 mL) and heptane (15 mL) are added, and the resulting mixture is extracted. The organic phase is washed with 15 mL of a 10% aqueous solution of sodium hydrogen sulphate followed by water (15 mL) and 10% aqueous sodium bicarbonate solution. The organic phase is removed in vacuum to give e.g. 0.18 g of the lactol XVIIIa M$^+$+=536.

Synthesis of (2R,3S,5S)-3-isopropyl-5-((2S,4S)-4-isopropyl-5-oxo-tetrahydro-furan-2-yl)-3-isopropyl-2-[4-methoxy-3-(3-methoxypropoxy)-phenyl]-pyrrolidine-1-carboxylic acid tert-butyl ester XIXa A solution of 0.16 g of alcohol XVIa in 3 mL of methylene chloride is treated with 0.005 g of TEMPO followed by portionwise addition of 0.20 g of (diacetoxyiodo)benzene. The mixture is stirred for 5 hours at room temperature after which time only lactol XVIIIa can be detected. A further 0.20 g of diacetoxyiodo benzene is added and the reaction stirred for a further 24 hours at room temperature. Aqueous sodium thiosulphate solution (5 mL of 10%) and water (5 mL) are added and the phases are separated. The organic phase is washed with 10 mL of water and the solvent is removed in vacuum to give an oil. Chromatography on silica-gel gives e.g. 0.12 g of XIXa.

Synthesis of (2R,3S,5S)-5-[(1S,3S)-3-(2-carbamoyl-2-methyl-propylcarbamoyl)-1-hydroxy-4-methyl-pentyl]-3-isopropyl-2-[4-methoxy-3-(3-methoxy-propoxy)-phenyl]-pyrrolidine-1-carboxylic acid tert-butyl ester XXIa

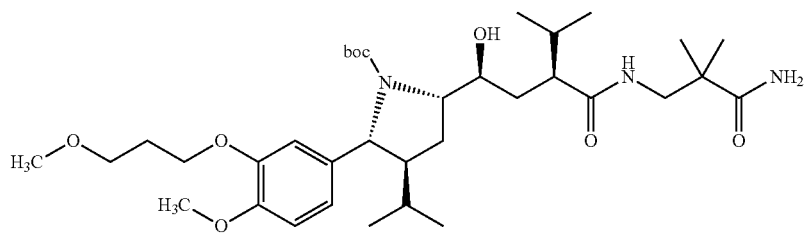

A solution of 0.08 g of lactone XIXa, 0.052 g of 3-amino-2,2-dimethylpropionamide and 0.014 g of 2-hydroxypyridine in 0.3 mL of tert-butylmethyl ether containing 0.02 g of triethylamine is stirred for 18 hours at 83° C. The reaction mixture is then cooled to room temperature and diluted with 2 mL of toluene and washed with 2 mL of 10% aqueous sodium hydrogen sulphate solution. The organic phase is separated and washed with water, and the solvent is removed in vacuum to give an oil. This oil is suspended in 5 mL of hexane and stirred. The solid is removed by filtration and the hexane removed in vacuum to give e.g. 0.06 g of amide XXIa as a foam. $M^+$-H=648.

Synthesis of ((1S,2S,4S)-4-(2-carbamoyl-2-methyl-propycarbamoyl)-2-hydroxy-1-{(S)-2-[4-methoxy-3-(3-methoxy-propoxy)-benzyl]-3-methylbutyl}-5-methyl-hexyl)-carbamic acid tert-butyl ester XXIIa

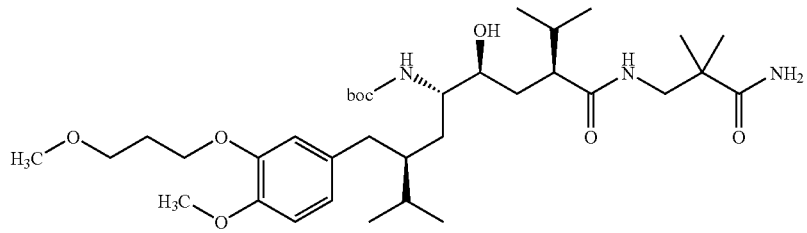

A solution of 0.037 g of amide XXIa is dissolved in 1 mL of tetrahydrofurane and cooled to −78° C. Liquid ammonia is added followed by 0.0042 g of lithium metal. The deep blue solution is stirred for 2 hours at −78° C., and then 0.35 g of ethanol is added and the mixture is stirred for 30 minutes at −78° C. Ammonium chloride (0.15 g) is added and the mixture is warmed to room temperature. The organic phase is partitioned between water and ethyl acetate. The organic phase is separated and the solvent removed in vacuum. The residue is stirred with heptane and filtered. Removal of the heptane produces XXIIa identical with an authentic sample. $M^++H=652$ (2S,4S,5S,7S)-5-amino-N-(2-carbamoyl-2-methyl-propyl)-4-hydroxy-2-isopropyl-7-[4-methoxy-3-(3-methoxypropoxy)benzyl]-8-methylnonanamide)

Product XXIIa is dissolved in a mixture of 4.0M hydrochloric acid in dioxane. The solution is stirred for 24 hours at room temperature and neutralized with solid sodium bicarbonate. The suspension is filtered and the solvent removed in vacuum to give the product as a foam (for characterization see e.g. EP 0 678 503, Example 137).

From the free compound or the hydrochloride salt obtainable, for example the hemifumarate salt of the title compound can be prepared, for example as described in U.S. Pat. No. 6,730,798, example J1 (comprising mixing with fumaric acid, dissolution in ethanol, filtration, evaporation of the obtained solution, re-dissolving of the residue in acetonitrile, inoculation with a small amount of the title compound's hemifumarate salt and isolation of the precipitating material), incorporated by reference herein especially with regard to this salt formation reaction.

Synthesis of ((1 S,2S,4S)-2-Hydroxy-4-hydroxymethyl-1-{(S)-2-[4-methoxy-3-(3-methoxy-propoxy)-benzyl]-3-methyl-butyl}-5-methyl-hexyl)-carbamic acid tert-butyl ester Compound XXV

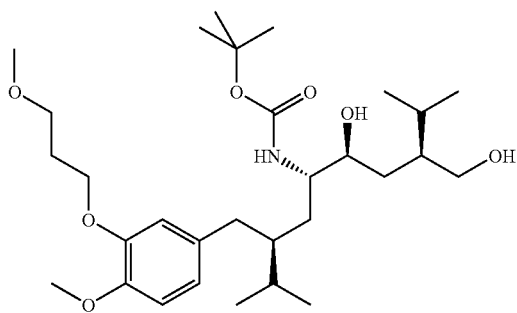

A solution of 1 g (1.59 mmol) of compound XVa in 17 mL of tetrahydrofuran is cooled to −78° C. and 17 mL of ammonia is added by condensation. Sodium metal (0.439 g, 19.08 mmol) is added and the solution is stirred at −78° C. for 24 hours. Ammonium chloride (2.56 g) is added and the temperature raised to room temperature. A mixture of toluene (40 mL) and acetic acid (1.9 g) is added and the solution stirred for 10 minutes at room temperature. Water (25 mL) is added and the organic phase separated. The aqueous phase is re-extracted with toluene (25 mL) and the combined organic phases washed 4 times with a 1/1 mixture of water and brine (total 480 mL). The organic layer is dried over anhydrous sodium sulphate and filtered. The solvent is removed in vacuum to give 0.86 g of the crude product. The crude product id purified by chromatography on silica-gel eluting with heptane/ethyl acetate mixtures to give 0.713 g of the pure compound. $^1$H-NMR (CDCl$_3$) δ 6.75 (2H, m, Ph), 6.71 (1 h, m, Ph), 4.68 (1H, Brd, NH), 4.10 (2H, t, CH$_2$O), 3.83 (3H, s, MeO), 3.59 (5H, m), 3.43 (1H, m, NCH), 3.36 (3H, s, MeO), 2.77 (1H, m, OH), 2.50 (3H, m, PhCH$_2$+OH), 2.10 (2H, m, CH$_2$), 1.75-1.56 (8H, m), 1.45 (9H, s, t-Bu), 0.91-0.86 (12H, m, 4×Me).

Synthesis of {(1S,3S)-1-((2S,4S)-4-Isopropyl-5-oxo-tetrahydro-furan-2-yl)-3-[4-methoxy-3-(3-methoxy-propoxy)-benzyl]-4-methyl-pentyl}-carbamic acid tert-butyl ester Compound XXVI

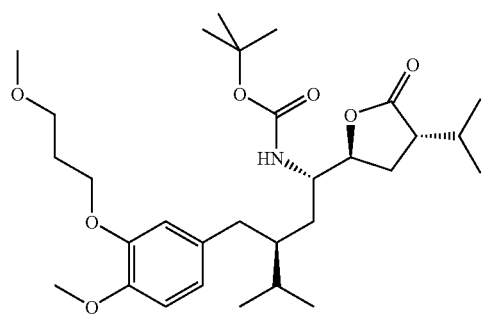

A solution of compound XXV (0.679 g, 1.26 mmol) in 12 mL of acetonitrile is treated sequentially with 0.7 g of powdered 4 A molecular sieves, 0.59 (5.04 mmol) of N-methylmorpholine N-oxide and 0.0442 g (0.126 mmol) of tetrapropylammonium perruthenate at room temperature. The mixture is stirred for 24 hours at room temperature and the solvent removed in vacuum. The residue is re-dissolved in ethyl acetate (20 mL) and filtered through a bed of silica-gel. The silica-gel is washed with ethyl acetate (900 mL) and the combined organic solutions evaporated to dryness to give 0.72 g of an oil. This oil is chromatographed on silica-gel eluting with heptane/ethyl acetate mixtures to give, after combination of the product fractions and removal of the solvent, 0.574 g of compound XXVI. $^1$H-NMR (CDCl$_3$) δ 6.80-6.65 (3H, m, Ph), 4.39 (1H, d, CHO-lactone), 4.10 (2H, t, CH$_2$O), 3.83-3.75 (4H, m, MeO+NCH), 3.59 (2H, m), 3.36 (3H, s, MeO), 2.64 (1H, dd, PhCH), 2.55 (1H, m, CHCO-lactone), 2.40 (1H, dd, PhCH), 2.21-2.05 (7H, m), 1.68 (4H, m), 1.45 (9H, s, t-Bu), 1.05 (3H, d, Me), 0.93 (3H, d, Me), 0.83 (6H, m, 2×Me).

Conversion of Compound XXVI to Compound XXIIa

Synthesis of ((1S,2S,4S)-4-(2-carbamoyl-2-methyl-propycarbamoyl)-2-hydroxy-1-{(S)-2-[4-methoxy-3-(3-methoxypropoxy)-benzyl]-3-methylbutyl}-5-methyl-hexyl)-carbamic acid tert-butyl ester XXIIa A solution of compound XXVI (0.108 g, 0.201 mmol) in 0.4 mL of tert-butylmethyl ether containing 70 mg of aminodimethylpropionamide, 19 mg of dimethylaminopyridine and 22 mg of triethylamine is heated to 73° C. for 24 hours. The reaction mixture is then cooled to room temperature and diluted with 5 mL of methylene chloride. The organic solution is washed with 10% aqueous sodium hydrogen sulphate and 2 mL of water. The organic layer is separated and dried and the solvent removed. The residue is re-dissolved in hot tert-butylmethyl ether and heptane is added to induce crystallisation. The suspension is cooled to 0° C. and stirred for 1 hour before filtration, washing and drying. Isolated is 84.5 mg of the desired compound XXIIa as a white solid. $^1$H-NMR (dmso D6) δ 7.45 (1H, Brt, NH), 7.15 (1H, Brs, NH), 6.90-

6.75 (3H, m, Ph), 6.65 (1H, d, NH), 6.25 (1H, d, NH), 4.38 (1H, d, OH), 3.96 (2H, t, CH$_2$O), 3.75 (3H, s, MeO), 3.55-3.45 (3H, m), 3.36-3.10 (6H, m), 2.64 (1H, dd, PhCH), 2.25 (2H, m), 1.95 (2H, m), 1.80-1.30 (17H, m), 1.10 (6H, s, 2×Me), 0.85 (6H, d, Me), 0.78 (6H, m, 2×Me). Rotation (1% in chloroform) 365 nM, −46.9°, 436 Nm, −32.7°, 546 Nm, −20.6°, 578 Nm, −18.1°, 589 Nm, −17.5°.

The invention claimed is:

1. A process for the manufacture of a compound of formula IV

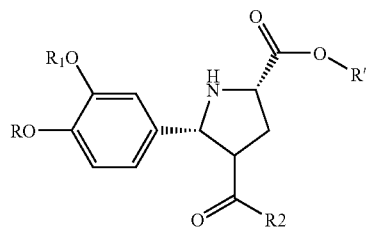

(IV)

wherein

R is hydrogen, alkyl or alkoxyalkyl;

R$_1$ is hydrogen, alkyl or alkoxyalkyl;

R$_2$ is alkyl and R' is alkyl or aralkyl, or a salt thereof, said manufacture comprising subjecting a compound of formula III

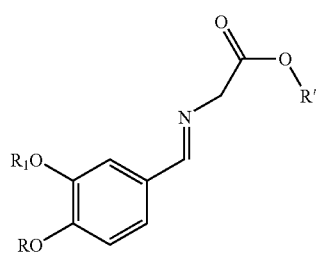

(III)

wherein R, R$_1$, R', and R$_2$ are as defined above in formula IV to a cycloaddition reaction with an α,β-unsaturated carbonyl species of formula (V)

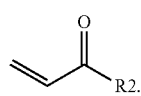

(V)

2. A compound of formula IV

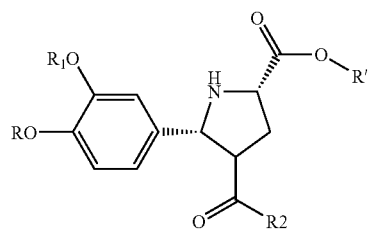

(IV)

wherein

R is hydrogen, alkyl or alkoxyalkyl;

R$_1$ is hydrogen, alkyl or alkoxyalkyl;

R$_2$ is alkyl, R' is alkyl or aralkyl;

or a salt thereof.

3. A compound of claim 2 having a structure of formula VIA

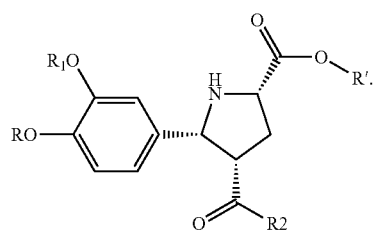

(VIA)

4. A compound of claim 2 with the name (2S,4S,5R)-4-Acetyl-5-[4-methoxy-3-(3-methoxy-propoxy)-phenyl]-pyrrolidine-2-carboxylic acid ethyl ester, or a salt thereof.

5. A process for the manufacture of a compound of formula VI (VI)

wherein R, R$_1$, R', and R$_2$ are as defined for the compound of the formula IV in claim 1 and PG is an amino protecting group removable by hydrolysis, or a salt thereof, said manufacture comprising introducing an amino protecting group on the pyrrolidine nitrogen of a compound of formula IV.

6. A compound of formula VI

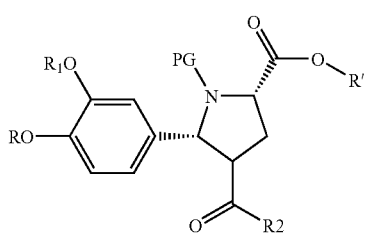

(VI)

wherein

R is hydrogen, alkyl or alkoxyalkyl;

$R_1$ is hydrogen, alkyl or alkoxyalkyl;

$R_2$ is alkyl;

R' is alkyl or aralkyl;

PG is an amino protecting group which is removable by hydrolysis, or a salt thereof.

7. A compound of claim 6 having a structure of formula VIA

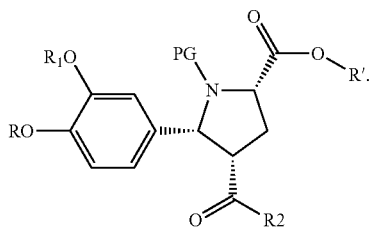

(VIA)

8. A compound of claim 5 with the name (2S,4S,5R)-4-Acetyl-5-[4-methoxy-3-(3-methoxy-propoxy)-phenyl]-pyrrolidine-1,2-dicarboxylic acid 1-tert-butyl ester 2-ethyl ester.

9. A process for the manufacture of a compound of formula VII (VII)

wherein R, $R_1$, R', and $R_2$ are as defined for the compound of the formula IV in claim 1 and PG is an amino protecting group removable by hydrolysis, or a salt thereof, said manufacture comprising conversion of the carbonyl of a compound of the formula VI as

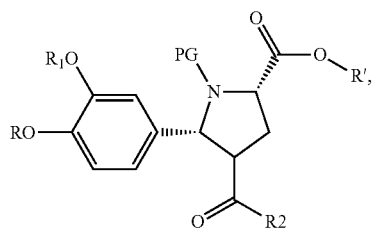

(VI)

wherein R, $R_1$, R', and $R_2$ are as defined for the compound of the formula IV in claim 1 and PG is an amino protecting group which is removable by hydrolysis to an olefin.

10. A compound of formula VII

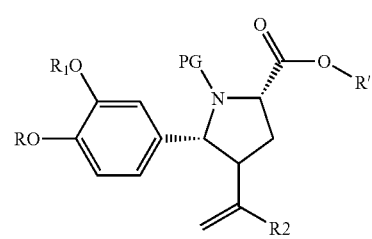

(VII)

wherein

R is hydrogen, alkyl or alkoxyalkyl;

$R_1$ is hydrogen, alkyl or alkoxyalkyl;

$R_2$ is alkyl;

R' is alkyl or aralkyl;

PG is an amino protecting group which is removable by hydrolysis or a salt thereof.

11. A compound of claim 10 having a structure of formula VIIA

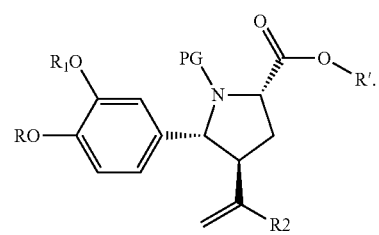

(VIIA)

12. A compound of claim 9 with the name (2S,4R,5R)-4-Isopropenyl-5-[4-methoxy-3-(3-methoxy-propoxy)-phenyl]-pyrrolidine-1,2-dicarboxylic acid 1-tert-butyl ester 2-ethyl ester.

13. A process for the manufacture of a compound of formula VIII

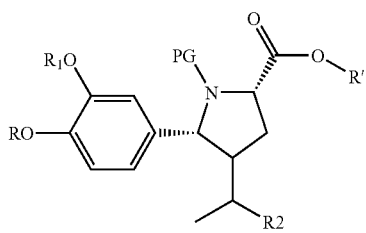
(VIII)

wherein R, $R_1$, R', and $R_2$ are as defined for the compound of the formula IV in claim 1 and PG is an amino protecting group removable by hydrolysis, or a salt thereof, said manufacture comprising hydrogenation of the olefin of a compound of the formula VII

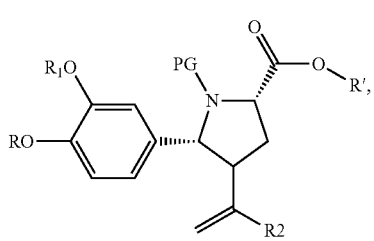
(VII)

wherein R, $R_1$, R', and $R_2$ are as defined for the compound of the formula IV in claim 1 and PG is an amino protecting group which is removable by hydrolysis.

14. A compound of formula VIII

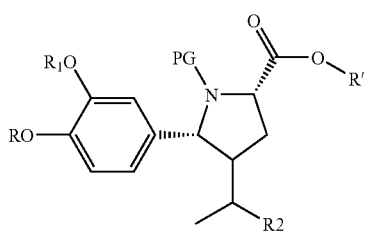
(VIII)

wherein
R is hydrogen, alkyl or alkoxyalkyl;
$R_1$ is hydrogen, alkyl or alkoxyalkyl;
$R_2$ is alkyl;
R' is alkyl or aralky;
PG is an amino protecting group which is removable by hydrolysis or a salt thereof.

15. A compound of claim 14 having a structure of formula VIIIA

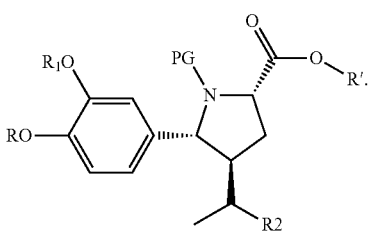
(VIIIA)

16. A compound of claim 14 with the name (2S,4S,5R)-4-Isopropyl-5-[4-methoxy-3-(3-methoxy-propoxy)-phenyl]-pyrrolidine-1,2-dicarboxylic acid 1-tert-butyl ester 2-ethyl ester.

17. A process for the manufacture of a compound of formula IX

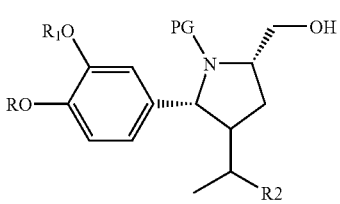
(IX)

wherein R, $R_1$, R', and $R_2$ are as defined for the compound of the formula IV in claim 1 and PG is an amino protecting group removable by hydrolysis, or a salt thereof, said manufacture comprising reduction of the ester moiety of a compound of the formula VIII

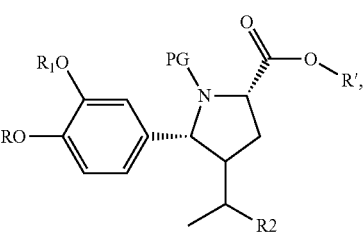
(VIII)

wherein R, $R_1$, R', and $R_2$ are as defined for the compound of the formula IV in claim 5 and PG is an amino protecting group which is removable by hydrolysis to an alcohol.

18. A process for the manufacture of a compound of formula XII

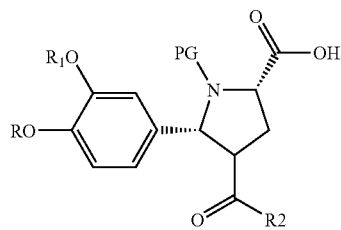

(XII)

wherein R, $R_1$, R', and $R_2$ are as defined for the compound of the formula IV in claim 1 and PG is an amino protecting group removable by hydrolysis, said manufacture comprising hydrolysis of the ester moiety of a compound of the formula VI

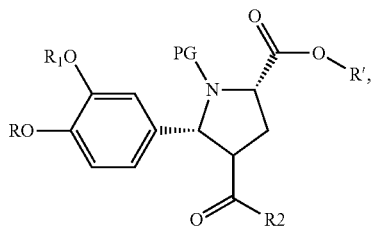

(VI)

wherein R, $R_1$, R', and $R_2$ are as defined for the compound of the formula IV in claim 1 and PG is an amino protecting group which is removable by hydrolysis to an acid.

19. A process for the manufacture of a compound of formula XIII

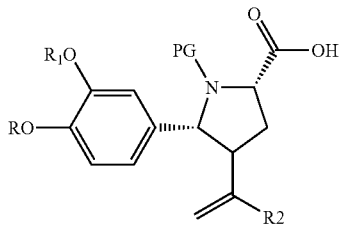

(XIII)

wherein R, $R_1$, R', and $R_2$ are as defined for the compound of the formula IV in claim 1 and PG is an amino protecting group removable by hydrolysis, said manufacture comprising hydrolysis of the ester moiety of a compound of the formula VII

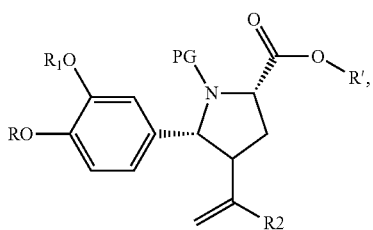

(VII)

wherein R, $R_1$, R', and $R_2$ are as defined for the compound of the formula IV in claim 1 and PG is an amino protecting group which is removable by hydrolysis to an acid.

* * * * *